US010660939B2

(12) United States Patent
Spana et al.

(10) Patent No.: US 10,660,939 B2
(45) Date of Patent: May 26, 2020

(54) THERAPIES FOR OBESITY, DIABETES AND RELATED INDICATIONS

(71) Applicant: Palatin Technologies, Inc., Cranbury, NJ (US)

(72) Inventors: Carl Spana, West Harrison, NY (US); John H. Dodd, Spring Mills, PA (US); Marie Makhlina, Highland Park, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 117 days.

(21) Appl. No.: 15/723,755

(22) Filed: Oct. 3, 2017

(65) Prior Publication Data

US 2018/0153965 A1    Jun. 7, 2018

Related U.S. Application Data

(63) Continuation of application No. PCT/US2016/027402, filed on Apr. 14, 2016.

(60) Provisional application No. 62/147,256, filed on Apr. 14, 2015.

(51) Int. Cl.
| | |
|---|---|
| *A61K 38/26* | (2006.01) |
| *A61K 38/12* | (2006.01) |
| *A61K 9/00* | (2006.01) |
| *A61P 3/00* | (2006.01) |
| *A61P 3/04* | (2006.01) |
| *A61P 3/10* | (2006.01) |

(52) U.S. Cl.
CPC ............ *A61K 38/26* (2013.01); *A61K 9/0019* (2013.01); *A61K 38/12* (2013.01); *A61P 3/00* (2018.01); *A61P 3/04* (2018.01); *A61P 3/10* (2018.01)

(58) Field of Classification Search
CPC ................................. A61K 38/26; A61K 38/12
See application file for complete search history.

(56) References Cited

U.S. PATENT DOCUMENTS

| | | | |
|---|---|---|---|
| 4,938,763 A | 7/1990 | Dunn et al. | |
| 5,576,290 A | 11/1996 | Hadley | |
| 5,674,839 A | 10/1997 | Hruby et al. | |
| 6,432,438 B1 | 8/2002 | Shukla | |
| 6,579,968 B1 | 6/2003 | Blood et al. | |
| 6,673,767 B1 | 1/2004 | Brodbeck et al. | |
| 6,794,489 B2 | 9/2004 | Blood et al. | |
| 7,326,707 B2 | 2/2008 | Sharma et al. | |
| 7,354,923 B2 | 4/2008 | Sharma et al. | |
| 7,456,184 B2 | 11/2008 | Sharma et al. | |
| 7,662,771 B2 | 2/2010 | Herr et al. | |
| 7,834,017 B2 | 11/2010 | Burris et al. | |
| 7,947,841 B2 | 5/2011 | Jungheim et al. | |
| 7,964,601 B2 | 6/2011 | Sharma et al. | |
| 7,968,548 B2 | 6/2011 | Sharma et al. | |
| 8,298,561 B2 | 10/2012 | Alessi et al. | |
| 8,455,617 B2 | 6/2013 | Dodd et al. | |
| 8,455,618 B2 | 6/2013 | Dodd et al. | |
| 8,487,073 B2 | 7/2013 | Shi et al. | |
| 8,492,517 B2 | 7/2013 | Yang et al. | |
| 8,729,224 B2 | 5/2014 | Shi et al. | |
| 8,846,601 B2 | 9/2014 | Shi et al. | |
| 8,877,890 B2 | 11/2014 | Yang et al. | |
| 8,912,226 B2 | 12/2014 | Grosch et al. | |
| 8,933,194 B2 | 1/2015 | Yang et al. | |
| 9,089,538 B2 | 7/2015 | Neerup et al. | |
| 9,156,901 B2 | 10/2015 | Riber | |
| 9,186,392 B2 | 11/2015 | Klein | |
| 9,205,081 B2 | 12/2015 | Toledano | |
| 9,278,123 B2 | 3/2016 | Sauerberg et al. | |
| 2003/0032791 A1 | 2/2003 | Robertson et al. | |
| 2009/0142338 A1 | 6/2009 | Levetan et al. | |
| 2009/0156474 A1 | 6/2009 | Roth et al. | |
| 2011/0256130 A1 | 10/2011 | Schultz et al. | |
| 2012/0077957 A1 | 3/2012 | Chen et al. | |
| 2012/0178670 A1 | 7/2012 | Riber | |
| 2013/0030417 A1 | 1/2013 | Alessi et al. | |
| 2013/0090278 A1 | 4/2013 | Alessi et al. | |
| 2013/0157929 A1 | 6/2013 | Riber et al. | |
| 2013/0157935 A1 | 6/2013 | Meier et al. | |
| 2013/0157953 A1 | 6/2013 | Petersen et al. | |
| 2013/0316005 A1 | 11/2013 | Pelaez et al. | |
| 2013/0316941 A1 | 11/2013 | Hamprecht et al. | |
| 2014/0031287 A1 | 1/2014 | Herr et al. | |
| 2014/0080757 A1 | 3/2014 | Tolborg | |
| 2014/0128402 A1 | 5/2014 | Pareek et al. | |
| 2014/0336107 A1 | 11/2014 | Tolborg et al. | |
| 2014/0357575 A1* | 12/2014 | Shi ...................... | C07K 5/1024 514/21.1 |

(Continued)

FOREIGN PATENT DOCUMENTS

| | | |
|---|---|---|
| EP | 1 792 626 A1 | 6/2007 |
| EP | 2 127 676 A2 | 12/2009 |

(Continued)

OTHER PUBLICATIONS

Clemmensen et al., EMBO Mol. Med. 7: 288-298, 2015.*
Clemmensen, "Dual melanocortin-4 receptor and GLP-1 receptor agonism amplifies metabolic benefits in diet-induced obese mice", EMBO Molecular Medicine, Feb. 4, 2015, 1-12.
Communication, "International Search Report and Written Opinion PCT/US16/27402", dated Nov. 29, 2016.
Deshmane, et al., "Monocyte Chemoattractant Protein-1 (MCP-1): An Overview", Journal of Interferon & Cytokine Research (vol. 29 N. 6), Dec. 5, 2008, 313-326.
Finan, "Emerging opportunities for the treatment of metabolic diseases: Glucagon-like peptide-1 based multi-agonists", Molecular and Cellular Endocrinology (418), Jul. 4, 2015, 42-54.

(Continued)

*Primary Examiner* — Gyan Chandra
(74) *Attorney, Agent, or Firm* — Stephen A. Slusher

(57) ABSTRACT

The invention relates to methods, uses, compositions and formulations including a melanocortin receptor-4 agonist and a glucagon-like peptide-1 receptor agonist for treatment of obesity, diabetes, metabolic syndrome and related indications, diseases or disorders.

17 Claims, 7 Drawing Sheets

Specification includes a Sequence Listing.

(56) References Cited

U.S. PATENT DOCUMENTS

| | | |
|---|---|---|
| 2015/0025003 A1 | 1/2015 | Spetzler et al. |
| 2015/0111817 A1 | 4/2015 | Riber et al. |
| 2015/0273021 A1* | 10/2015 | Kaplan .................. A61K 47/42 514/7.2 |
| 2016/0051511 A1 | 2/2016 | Ochoa |
| 2016/0067184 A1 | 3/2016 | Nielsen et al. |

FOREIGN PATENT DOCUMENTS

| | | |
|---|---|---|
| EP | 2 496 249 B1 | 3/2016 |
| WO | 2005/072045 A2 | 8/2005 |
| WO | 2006/049933 A2 | 5/2006 |
| WO | 2006/134340 A2 | 12/2006 |
| WO | 2007/100535 A2 | 9/2007 |
| WO | 2008/010101 A2 | 1/2008 |
| WO | 2008/152403 A1 | 12/2008 |
| WO | 2009/155257 A1 | 12/2009 |
| WO | 2009/155258 A2 | 12/2009 |
| WO | 2010/070251 A1 | 6/2010 |
| WO | 2010/070252 A1 | 6/2010 |
| WO | 2010/070253 A1 | 6/2010 |
| WO | 2010/070255 A1 | 6/2010 |
| WO | 2010/144341 A2 | 12/2010 |
| WO | 2010/144344 A2 | 12/2010 |
| WO | 2011/006497 A1 | 1/2011 |
| WO | 2011/160630 A2 | 12/2011 |
| WO | 2011/160633 A1 | 12/2011 |
| WO | 2013/064669 A1 | 5/2013 |
| WO | 2013/092703 A2 | 6/2013 |
| WO | 2014/041195 A1 | 3/2014 |
| WO | 2014/144260 A1 | 9/2014 |
| WO | 2014/144842 A2 | 9/2014 |
| WO | 2014/160016 A2 | 10/2014 |
| WO | 2015/001573 A9 | 1/2015 |
| WO | 2015/022400 A1 | 2/2015 |
| WO | 2015/055802 A2 | 4/2015 |
| WO | 2015/116729 A2 | 8/2015 |
| WO | 2015/121413 A1 | 8/2015 |
| WO | 2015/155139 A1 | 10/2015 |
| WO | 2015/155140 A1 | 10/2015 |
| WO | 2015/155141 A1 | 10/2015 |
| WO | 2015/155151 A1 | 10/2015 |
| WO | 2015/170286 A2 | 11/2015 |
| WO | 2015/193378 A1 | 12/2015 |
| WO | 2015/193381 A1 | 12/2015 |
| WO | 2016/046753 A1 | 3/2016 |
| WO | 2016/154014 A1 | 9/2016 |

OTHER PUBLICATIONS

Hadley, et al., "The Proopiomelanocortin System", Annals New York Academy of Sciences, 1999, 1-21.

Hansen, "The DPP-IV inhibitor Linagliptin and GLP-1 indice synergistic effects on body weight loss and appetite suppression in the diet-induced obese rat", European Journal of Pharmacology (741), Aug. 24, 2014, 254-263.

Hsiung, et al., "A Novel and Selective β-Melanocyte-Stimulating Hormone-Derived Peptide Agonist for Melanocotine 4 Receptor Potently Decreased Food Intake and Body Weight Gain in Diet-Induced Obese Rats", Endocrinology 146(12), Sep. 15, 2005, 5257-5266.

Maida, et al., "The Glucagon-Like Peptide-1 Receptor Agonist Oxyntomodulin Enhances β-Cell Function but Does Not Inhibit Gastric Emptying in Mice", Endocrinology 149(11), Jul. 31, 2008, 5670-5678.

Minokoshi, et al., "Role of hypothalamic AMP-kinase in food intake regulation", Nutrition (24), Jun. 3, 2008, 786-790.

Nonogaki, et al., "The contribution of serotonin 5-HT2C and melanocortin-4 receptors to the satiety signaling of glucagon-like peptide 1 and liragultide, a glucagon-like peptide 1 receptor agonist, in mice", Biochemical and Biophysical Research Communications (411), Jul. 2, 2011, 445-448.

Patel, "Combination of omeprazol with GLP-1 agonist therapy improves insulin sensitivity and antioxidant activity in liver in type 1 diabetic mice", Pharmacological Reports (65), 2013, 927-936.

Poleni, "Possible involvement of melanocortin-4-receptor and AMP-activated protein kinase in the interaction of glucagon-like peptide-1 and leptin on feeding in rats", Biochemical and Biophysical Research Communications (420), Feb. 27, 2012, 36-41.

Trujillo, et al., "GLP-1 receptor agonists: a review of head-to-head clinical studies", Ther Adv Endocrinol Metal vol. 6(1), 2015, 19-28.

* cited by examiner

SEQUENCE LISTING

<160> NUMBER OF SEQ ID NOS: 3

<210> SEQ ID NO 1
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 1

His Ala Glx Gly Thr Phe Thr Ser Asx Val Ser Ser Tyr Leu Glx Gly
 1               5                  10                  15

Glx Ala Ala Lys Glx Phe Ile Ala Trp Leu Val Lys Gly Arg
            20                  25                  30

```
-continued

<210> SEQ ID NO 2
<211> LENGTH: 13
<212> TYPE: PRT
<213> ORGANISM: Artificial Sequence
<220> FEATURE:
<223> OTHER INFORMATION: Synthetic melanocortin binding peptide derived
      from human alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 2

Ser Tyr Ser Met Glu His Phe Arg Trp Gly Lys Pro Val
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic melanocortin binding peptide derived
      from human alpha-MSH

<400> SEQUENCE: 3

His Phe Arg Trp
1
```

THERAPIES FOR OBESITY, DIABETES AND RELATED INDICATIONS

CROSS-REFERENCE TO RELATED APPLICATION

This application is a continuation application of International Application No. PCT/US2016/027402, published as International Publication No. WO 2016/168388, entitled "Therapies for Obesity, Diabetes and Related Indications", filed Apr. 14, 2016, which in turn claims priority to and the benefit of the filing of U.S. Provisional Patent Application Ser. No. 62/147,256 entitled "Therapies for Obesity, Diabetes and Related Indications", filed Apr. 14, 2015, and the specification and claims thereof are incorporated herein by reference.

BACKGROUND OF THE INVENTION

Field of the Invention (Technical Field)

The present invention relates to medical use of compounds specific for melanocortin receptors and compounds specific for glucagon-like peptide-1 receptors, for example in the treatment of obesity, diabetes, metabolic syndrome and related indications, diseases or disorders.

Description of Related Art

The following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin receptor-1 (MC1r) expressed on normal human melanocytes, melanoma cells and other cells; melanocortin receptor-2 (MC2r) for ACTH (adrenocorticotropin), expressed in cells of the adrenal gland; melanocortin receptor-3 and melanocortin receptor-4 (MC3r and MC4r), expressed in cells in the hypothalamus, mid-brain, brainstem and in peripheral tissues; and melanocortin receptor-5 (MC5r), expressed in a wide distribution of peripheral tissues. MC1r is believed to be associated with hair and skin pigmentation, mediation of inflammation and other functions; MC2r is believed to mediate steroidogenesis; MC3r is believed to be associated with energy homeostasis, food intake, and inflammation; MC4r is believed to be associated with feeding behavior, energy homeostasis, and sexual functioning; and MC5r is believed to be involved in exocrine gland system regulation and other functions.

Significant work has been done in determining the structure of melanocortin receptors, including both the nucleic acid sequences encoding for the receptors and the amino acid sequences constituting the receptors. MC4r is a G protein-coupled, 7-transmembrane receptor that is expressed in the brain, particularly the paraventricular nucleus of the hypothalamus and the dorsal motor nucleus of the vagus nerve within the hindbrain, but is also expressed peripherally, including intestinal cells.

MC4r inactivation has been shown to result in obesity (Hadley, *Ann N Y Acad Sci,* 885:1-21 (1999)), with activation of MC4r, through the endogenous agonist α-melanocyte stimulating hormone (α-MSH) or synthetic analogs, resulting in weight loss (Hsiung et al., *Endocrinology,* 146:5257-5266 (2005)). Agouti-related protein (AgRP) is an endogenous compound that has been suggested to be an antagonist or an inverse agonist on MC4r. α-MSH is believed to be the principle endogenous MC4r agonist.

Peptides specific for MC4r, including MC4r agonists, and secondarily peptides specific for MC3r, are believed to be useful in regulation of mammalian energy homeostasis, including use as agents for attenuating food intake and body weight gain.

Melanocortin receptor-specific cyclic peptides include α-MSH analog peptides such as Ac-Nle-cyclo(-Asp-His-D-Phe-Arg-Trp-Lys)-$NH_2$ (See U.S. Pat. Nos. 5,674,839 and 5,576,290) and Ac-Nle-cyclo(-Asp-His-D-Phe-Arg-Trp-Lys)-OH (See U.S. Pat. Nos. 6,579,968 and 6,794,489). These and other melanocortin receptor-specific peptides generally contain the central tetrapeptide sequence of native α-MSH, $His^6$-$Phe^7$-$Arg^8$-$Trp^9$, or a mimetic or variation thereof, such as the substitution of D-Phe for $Phe^7$. Other melanocortin receptor-specific cyclic peptides, including primarily MC4r specific peptides, are disclosed in U.S. Pat. Nos. 7,326,707; 7,354,923; 7,456,184; 7,834,017; 7,964,601; 7,968,548; 8,455,617; 8,455,618; 8,487,073; 8,492,517; 8,729,224; 8,846,601; 8,877,890; and 8,933,194; and applications US 2012/0077957 and US 2014/0357575. Melanocortin receptor-specific cyclic peptides disclosed in the foregoing are typically cyclized through a lactam bridge, or alternatively through a disulfide bridge formed by the side chains of two Cys or other reactive thiol-containing residues.

Also known are glucagon analogs and compounds related to glucagon, including pre-proglucagon, glucagon, glucagon-like peptide-1 (GLP-1), glucagon-like peptide-2 (GLP-2) and oxyntomodulin (OXM). Pre-proglucagon is a 179 amino acid precursor polypeptide. Proglucagon is a 158 amino acid precursor polypeptide that is differentially processed in vivo to form glucagon, GLP-1, GLP-2, and OXM. GLP-1, GLP-2 and OXM molecules are involved in a wide variety of physiological functions, including glucose homeostasis, insulin secretion, gastric emptying and intestinal growth, as well as regulation of food intake.

Glucagon is a 29-amino acid peptide that corresponds to amino acids 53 to 81 of proglucagon. OXM is a 37 amino acid peptide which includes the complete 29 amino acid sequence of glucagon with an octapeptide carboxyterminal extension (amino acids 82 to 89 of pre-proglucagon). Human GLP-1 is a 30- or 31-amino acid peptide, generally C-terminally amidated, of the structure H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-$NH_2$ (SEQ ID NO:1) (30 amino acid, with the 31 amino acid variant having a C-terminal Gly-OH). GLP-1 is believed to increase insulin secretion from the pancreas in a glucose-dependent manner; decrease glucagon secretion from the pancreas by engagement of a specific G protein-coupled receptor; increase insulin-sensitivity in both alpha cells and beta cells; increase beta cells mass and insulin gene expression, post-translational processing and incretion; inhibit acid secretion and gastric emptying in the stomach; decrease food intake by increasing satiety in the brain; and promote insulin sensitivity.

There are a number of GLP-1 receptor agonists which have been approved for pharmaceutical use in one or more, including exenatide, sold under the trade names Byetta® and Bydureon®; liraglutide, sold under the trade names Victoza® and Saxenda®; lixisenatide, sold under the trade name Lyxumia®; albiglutide, sold under the trade name Tanzeum®; and dulaglutide, sold under the trade name Trulicity®. Exenatide is an incretin mimetic which is a synthetic version of exendin-4, a hormone found in the saliva of the Gila monster. Liraglutide, also an incretin mimetic, is a derivative of GLP-1. Lixisenatide, also an incretin mimetic, is derived from the first 39 amino acids in the sequence of exendin-4, omitting proline at position 38 and adding six lysine residues. Albiglutide is a dipeptidyl peptidase-4-resistant GLP-1 dimer fused to human albumin. Dulaglutide is a fusion protein consisting of two identical, disulfide-linked chains, with each chain including a modified N-terminal GLP-1 analog sequence covalently linked to the Fc portion of a modified human immunoglobulin heavy chain by a peptide linker. The foregoing approved GLP-1 receptor agonists are all peptides or small proteins, and are administered typically by subcutaneous injection. Some require daily injections; others can be injected at weekly or longer intervals.

While both GLP-1 receptor agonists and MC4r agonists have utility in treatment of obesity, diabetes mellitus type 2, metabolic syndrome and other conditions, there are limitations on the utility of each, particularly for treatment of obesity, metabolic syndrome and related indications. It is against this background that the present invention was made.

BRIEF SUMMARY OF THE INVENTION

The invention provides a pharmaceutical composition for subcutaneous administration in treatment of obesity or to induce weight loss, comprising on a per dose basis:

a MC4r agonist in a quantity sufficient to induce at least minimal weight loss when administered as a monotherapy not in conjunction with a GLP-1 receptor agonist; and a GLP-1 receptor agonist in a quantity sufficient to induce glycemic control but not weight loss when administered as a monotherapy not in conjunction with a MC4r agonist. The pharmaceutical composition preferably has a synergistic anti-obesity effect. In the composition formulated for once daily administration, the MC4r agonist may be Peptide No. 154 and the GLP-1 receptor agonist may be liraglutide, preferable between about 1.5 mg and 10 mg of Peptide No. 154 and between about 0.6 mg and 1.5 mg of liraglutide on a per dose basis. In the composition formulated for once daily administration, the MC4r agonist may be Peptide No. 154 and the GLP-1 receptor agonist may be exenatide, preferable between about 0.75 mg and 5 mg of Peptide No. 154 and between about 5 µg and 20 µg of exenatide on a per dose basis. The composition may further include either or both a pharmaceutically acceptable salt and a pharmaceutically acceptable carrier.

In another aspect, the invention provides a pharmaceutical composition comprising as components:

(a) a MC4r agonist, and
(b) a GLP-1 receptor agonist;

wherein components (a) and (b) are present in such weight or molar ratio that the composition exerts a synergistic effect in treatment of obesity or to induce weight loss upon administration to a patient. This composition may include at least one pharmaceutically acceptable carrier. If formulated for once daily administration, the MC4r agonist may be Peptide No. 154 and the GLP-1 receptor agonist may be liraglutide, such as between about 1.5 mg and 10 mg of Peptide No. 154 and between about 0.6 mg and 1.5 mg of liraglutide on a per dose basis. If formulated for twice daily administration, the composition may include between about 0.75 mg and 5 mg of Peptide No. 154 and between about 5 µg and 20 µg of exenatide on a per dose basis.

In another aspect, the invention provides a method of treating a patient with obesity, diabetes or metabolic syndrome, comprising administering to the patient (a) a MC4r agonist in a quantity sufficient to induce at least minimal weight loss when administered as a monotherapy not in conjunction with a GLP-1 receptor agonist and (b) a GLP-1 receptor agonist in a quantity sufficient to induce glycemic control but not weight loss when administered as a monotherapy not in conjunction with a MC4r agonist. Preferably the method elicits a synergistic effect on treatment of obesity. The quantity and schedule of administration of the MC4r agonist and the GLP-1 receptor agonist may together be sufficient to produce synergistic effect in the treatment of obesity. Alternatively or additionally, the method elicits a synergistic effect on treatment of glycemic control. The quantity and schedule of administration of the MC4r agonist and the GLP-1 receptor agonist may together be sufficient to produce synergistic effect in the treatment of glycemic control. In the method, the MC4r agonist may be Peptide No. 154 administered daily by subcutaneous injection and the GLP-1 receptor agonist may be administered by subcutaneous injection. The GLP-1 receptor agonist may be liraglutide or exenatide administered daily or twice daily, or may be lixisenatide, albiglutide, dulaglutide or an extended release formulation of exenatide or liraglutide administered at weekly or greater intervals. The MC4r agonist and the GLP-1 receptor agonist may be administered simultaneously to the patient, sequentially to the patient in either order or via different pathways of administration. In the method, either or both the MC4r agonist and the GLP-1 may be sustained, including a sustained-released GLP-1 receptor agonist with a duration of action of at least about twenty-four hours, at least about one week or at least about two weeks. In a related aspect, the MC4r agonist is not sustained-release.

In another aspect, the invention provides a method of decreasing side effects associated with therapeutic agents for treatment of obesity, diabetes or metabolic syndrome in a patient, comprising:

administration of a quantity of MC4r agonist, wherein the quantity of MC4r agonist administered, if administered as a monotherapy not in conjunction with GLP-1 receptor agonist, is not sufficient to initiate the desired pharmacological response in treating at least one condition from the group comprising obesity, diabetes and metabolic syndrome in the patient when administered as a monotherapy; and administration of a quantity of GLP-1 receptor agonist, wherein the quantity of GLP-1 receptor agonist administered, if administered as a monotherapy not in conjunction with MC4r agonist, is not sufficient to initiate the desired pharmacological response in treating at least one condition from the group comprising obesity, diabetes and metabolic syndrome in the patient when administered as a monotherapy;

wherein the quantity of the MC4r agonist and the quantity of GLP-1 receptor agonist are together effective to initiate the desired pharmacological response treating at least one condition from the group comprising obesity, diabetes and metabolic syndrome in the patient, thereby reducing side effects in the treatment of at least one of obesity, diabetes or metabolic syndrome in the patient.

In the practice of this method, the quantity of MC4r agonist administered is in one aspect not sufficient to initiate the desired pharmacological response of inducing weight loss. In another aspect, the quantity of MC4r agonist administered is sufficient to induce minimal weight loss. The desired pharmacological response may be inducing weight loss or inducing glycemic control.

In another aspect, the invention provides a method of treating obesity or inducing weight loss in an obese patient, comprising the steps of:

establishing a dose of a GLP-1 receptor agonist which induces glycemic control in the patient but which induces no more than minimal weight loss in the patient;

administration of the dose of the GLP-1 receptor agonist; and administration of a MC4r agonist;

wherein the dose of the GLP-1 receptor agonist and the quantity of MC4r agonist are effective to treat obesity or to induce weight loss.

In this method, the dose of GLP-1 receptor agonist preferably does not induce minimal weight loss in the patient. The administration of the dose of the GLP-1 receptor agonist and administration of a MC4r agonist may be simultaneous, such as by means of a combination pharmaceutical composition comprising GLP-1 receptor agonist and MC4r agonist. In the practice of the method, the MC4r agonist may be Peptide No. 154 administered daily, such as by subcutaneous injection. The GLP-1 receptor agonist may also be administered by subcutaneous injection, such as liraglutide or exenatide administered daily or twice daily or lixisenatide, albiglutide, dulaglutide or an extended release formulation of exenatide or liraglutide administered at weekly or greater intervals. In the method, administration of the dose of the GLP-1 receptor agonist and administration of a MC4r agonist may elicit a synergistic effect on treatment of obesity, or may elicit a synergistic effect on inducing glycemic control, or both.

In another aspect, the present invention provides a combination therapeutic pharmaceutical composition for use in the treatment of obesity, diabetes and related indications, comprising a MC4r agonist and a GLP-1 receptor agonist.

In another aspect, the present invention provides combination therapy comprising a peptide-based melanocortin receptor-specific pharmaceutical, wherein the peptide is a selective MC4r agonist, together with a GLP-1 receptor agonist.

Other aspects and novel features, and the further scope of applicability of the present invention will be set forth in part in the detailed description to follow, and in part will become apparent to those skilled in the art upon examination of the following, or may be learned by practice of the invention. The aspects of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention.

DETAILED DESCRIPTION OF THE INVENTION

Definitions

Figure 1:
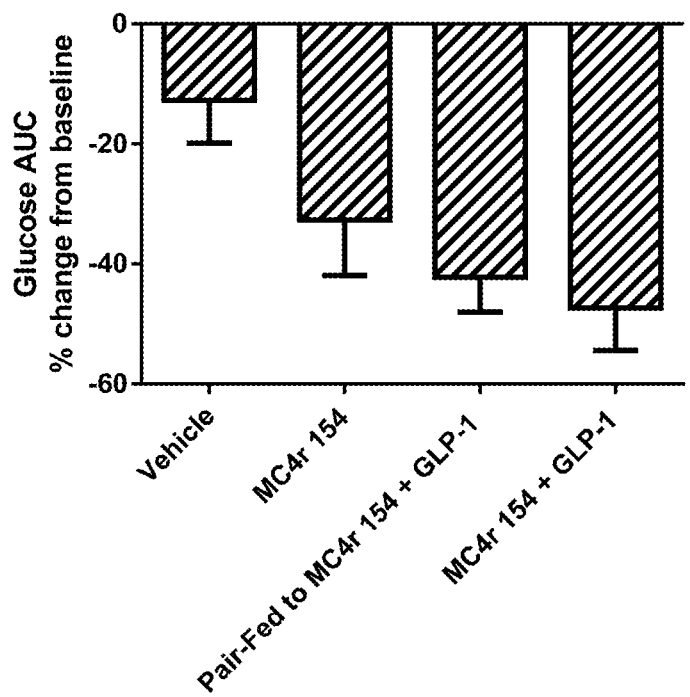
FIG. 1 depicts percent change in the area under the curve (AUC) for a glucose tolerance test from the baseline test to the termination test for diet induced obese (DIO) mice administered vehicle, an MC4r agonist (Peptide No. 154, hereafter "MC4r 154"), combinations of MC4r 154 and GLP-1, or GLP-1 with a caloric restriction to mimic food intake with MC4r 154, all±standard deviation (SD) from the baseline test. All compounds were administered via subcutaneous osmotic pump on study days 0 to 5. For combination therapy the agents were co-formulated into one solution and administered via a single osmotic pump. For the GLP-1 caloric restriction group the pump implantation was delayed by one day and the amount of food given to the animals was matched to those receiving MC4r 154 alone. The glucose tolerance test was conducted on day −2 (baseline) and day 6 (termination) by administering glucose orally at 1 g/kg and measuring blood glucose levels at various time points.

Before proceeding with the description of the invention, certain terms are defined as set forth herein.

In the sequences given for the peptides according to the present invention, the amino acid residues have their conventional meaning as given in Chapter 2400 of the *Manual* of *Patent Examining Procedure*, 9th Ed. Thus, "Ala" is alanine, "Asn" is asparagine, "Asp" is aspartic acid, "Arg" is arginine, "Cys" is cysteine, "Gly" is glycine, "Gln" is glutamine, "Glu" is glutamic acid, "His" is histidine, "Ile" is isoleucine, "Leu" is leucine, "Lys" is lysine, "Met" is methionine, "Phe" is phenylalanine, "Pro" is proline, "Ser" is serine, "Thr" is Threonine, "Trp" is tryptophan, "Tyr" is tyrosine, and "Val" is valine, and so on. It is to be understood that "D" isomers are designated by a "D-" before the three letter code or amino acid name, such that for example D-Phe is D-phenylalanine. Amino acid residues not encompassed by the foregoing have the following definitions:

| Abbreviation | Common Name | Side Chain or Amino Acid Structure |
|---|---|---|
| Aib | alpha-aminoisobutyric acid | |
| Aic | 2-aminoindane-2-carboxylic acid | |
| Cit | citrulline | |
| Dab | diaminobutyric acid | |
| Dab(Acetyl) | 2-amino, 4-acetylaminobutyric acid | |
| Dab(Glycyl) | 2-amino, 4-(glycyl) aminobutyric acid | |
| Dap | diaminoproprionic acid | |
| hGlu | homoglutamic acid | |
| Hyp | hydroxyproline | |

-continued

| Abbreviation | Common Name | Side Chain or Amino Acid Structure |
|---|---|---|
| Hyp(Bzl) | O-benzyl-hydroxyproline | |
| Met($O_2$) | Methionine sulfone | |
| Met(=O) | Methionine sulfoxide | |
| Nal 1 | 3-(1-naphthyl) alanine | |
| Nal 2 | 3-(2-naphthyl) alanine | |
| Nle | norleucine | |
| Orn | ornithine | |
| Phe(2-C(=O)—$NH_2$) | 2-carbamoyl-phenylalanine | |
| Phe(3-C(=O)—$NH_2$) | 3-carbamoyl-phenylalanine | |

-continued

| Abbreviation | Common Name | Side Chain or Amino Acid Structure |
|---|---|---|
| Phe(4-C(=O)—NH$_2$) | 4-carbamoyl-phenylalanine | |
| Pro(4R-Bzl) | 4(R)benzyl-proline | |
| Pro(4R—NH$_2$) | 4(R)amino-proline | |
| Sar | sarcosine | |
| Ser(Bzl) | O-benzyl-serine | |
| Thr(Bzl) | O-benzyl-threonine | |

By a melanocortin receptor "agonist" is meant an endogenous substance, drug substance or compound, including a compound such as the MC4r peptides disclosed herein, which can interact with a melanocortin receptor and initiate a pharmacological response, including but not limited to adenyl cyclase activation, characteristic of the melanocortin receptor. For the present invention, a melanocortin receptor agonist which is an agonist at melanocortin receptor-4 (MC4r agonist) is preferred.

By "α-MSH" is meant the peptide Ac-Ser-Tyr-Ser-Met-Glu-His-Phe-Arg-Trp-Gly-Lys-Pro-Val-NH$_2$ (SEQ ID NO:2) and analogs and homologs thereof, including without limitation NDP-α-MSH.

By "binding affinity" is meant the ability of a compound or drug to bind to its biological target, expressed herein as Ki (nM).

The term "combination therapy" is intended to mean the use of more than one active ingredient in treatment of any disease, condition or syndrome. A combination therapy may be a composition comprising more than one active ingredient, or may be the use of different compositions, which may be administered by the same or different routes of administration, with each composition including at least one, including only one, active ingredient. When combination therapy includes use of more than one composition, the compositions may be administered at the same time or at separate times, and thus combination therapy includes administration of different compositions separated by a number of hours or days.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

The term "diabetes" includes type 1 diabetes, which is insulin-dependent diabetes mellitus as diagnosed according to criteria published in the Report of the Expert Committee on the Diagnosis and Classification of Diabetes Mellitus (*Diabetes Care*, Vol. 24, Supp. 1, January 2001) whereby fasting plasma glucose level is greater than or equal to 126 milligrams per deciliter and for which the primary cause is pancreatic beta cell destruction, type 2 diabetes, which is non-insulin-dependent diabetes mellitus as diagnosed according to criteria published in the Report of the Expert Committee on the Diagnosis and Classification of Diabetes Mellitus whereby fasting plasma glucose level is greater than or equal to 126 milligrams per deciliter, and latent autoimmune diabetes mellitus of adults.

By "EC$_{50}$" is meant the molar concentration of an agonist, including a partial agonist, which produced 50% of the maximum possible response for that agonist. By way of example, a test compound which, at a concentration of 72 nM, produces 50% of the maximum possible response for that compound as determined in a cAMP assay in an MC4r cell expression system has an EC$_{50}$ of 72 nM. Unless otherwise specified, the molar concentration associated with an EC$_{50}$ determination is in nanomoles per liter (nM).

In general, "functional activity" is a measure of the signaling of a receptor, or measure of a change in receptor-associated signaling, such as a melanocortin receptor, and in particular MC4r or hMC4r, upon activation by a compound. Melanocortin receptors initiate signal transduction through activation of multimeric G proteins. GLP-1 receptor agonists also initiate signal transduction through activation of multimeric G proteins.

By "GLP-1 receptor agonist" is meant one or more naturally occurring GLP-1 receptor agonists, including GLP-1 polypeptides (GLP-1 (7-37)-OH and GLP-1 (7-36)-NH$_2$, GLP-1 fragments, GLP-1 analogs, GLP-1 derivatives of naturally occurring GLP-1 polypeptides, GLP-1 fragments, or GLP-1 analogs, and Exendin-3 and Exendin-4 that have the ability to bind to the GLP-1 receptor and initiate a signal transduction pathway resulting in insulinotropic activity, including but not limited to exenatide, liraglutide, lixisenatide, taspoglutide, albiglutide, and dulaglutide.

A compound is effective to "induce glycemic control" when the compound induces, over a period of time of 12 weeks or greater, a statistically significant and placebo-adjusted decrease in either (a) mean hemoglobin A$_{1c}$ or (b) mean fasting plasma glucose of at least about 5.0% in a cohort of subjects with a baseline mean hemoglobin A$_{1c}$ of at least about 7.5% or a baseline mean fasting plasma glucose of at least about 150 mg/dL.

By "inhibition" is meant the percent attenuation, or decrease in receptor binding, in a competitive inhibition assay compared to a known standard. Thus, by "inhibition at 1 µM (NDP-α-MSH)" is meant the percent decrease in binding of NDP-α-MSH by addition of a determined amount of the compound to be tested, such as 1 µM of a test compound, such as under the assay conditions hereafter described. By way of example, a test compound that does not inhibit binding of NDP-α-MSH has a 0% inhibition, and a test compound that completely inhibits binding of NDP-α-MSH has a 100% inhibition. Typically, as described hereafter, a radio assay is used for competitive inhibition testing, such as with $I^{125}$-labeled NDP-α-MSH, or a lanthanide chelate fluorescent assay, such as with Eu-NDP-α-MSH. However, other methods of testing competitive inhibition are known, including use of label or tag systems other than radioisotopes, and in general any method known in the art for testing competitive inhibition may be employed in this invention. It may thus be seen that "inhibition" is one measure to determine whether a test compound attenuates binding of NDP-α-MSH or α-MSH to melanocortin receptors.

By "intrinsic activity" is meant the maximal functional activity achievable by a compound in a specified melanocortin receptor expressing cell system, such as the maximal stimulation of adenylyl cyclase. The maximal stimulation achieved by α-MSH or NDP-α-MSH is designated as an intrinsic activity of 1.0 (or 100%), and a compound capable of stimulating half the maximal activity of α-MSH or NDP-α-MSH is designated as having an intrinsic activity of 0.5 (or 50%). A compound of this invention that under assay conditions described herein has an intrinsic activity of 0.7 (70%) or higher is classified as an agonist, and a compound with intrinsic activity less than 0.7 (70%) is classified as a partial agonist. In one aspect, the MC4r peptides utilized in the present invention may generally be characterized as an agonist at MC4r with respect to α-MSH or NDP-α-MSH.

By "Ki (nM)" is meant the equilibrium inhibitor dissociation constant representing the molar concentration of a competing compound that binds to half the binding sites of a receptor at equilibrium in the absence of radioligand or other competitors. In general, the numeric value of the Ki is inversely correlated to the affinity of the compound for the receptor, such that if the Ki is low, the affinity is high. Ki may be determined using the equation of Cheng and Prusoff (Cheng Y., Prusoff W. H., *Biochem. Pharmacol.* 22: 3099-3108, 1973):

$$Ki = \frac{EC_{50}}{1 + \frac{[ligand]}{K_D}}$$

where "ligand" is the concentration of radioligand and $K_D$ is an inverse measure of receptor affinity for the radioligand which produces 50% receptor occupancy by the radioligand. Unless otherwise specified, the molar concentration associated with a Ki determination is in nM. Ki may be expressed in terms of specific receptors (e.g., MC1r, MC3r, MC4r or MC5r) and specific ligands (e.g., α-MSH or NDP-α-MSH).

The term "metabolic syndrome" refers to metabolic disorders, particularly glucose and lipid regulatory disorders, including insulin resistance and defective secretion of insulin by pancreatic beta cells, and may further include conditions and states such as abdominal obesity, dyslipidemia, hypertension, glucose intolerance or a prothrombitic state, and which may further result in disorders such as hyperlipidemia, obesity, diabetes, insulin resistance, glucose intolerance, hyperglycemia, and hypertension.

A compound is effective to induce at least "minimal weight loss" when the compound induces, over a period of time from 12 to 52 weeks, a statistically significant and placebo-adjusted decrease in mean body weight of at least about 2.5%, but less than about 5.0%, in a cohort of subjects with a baseline mean BMI≥27 kg/m².

By "NDP-α-MSH" is meant the peptide Ac-Ser-Tyr-Ser-Nle-Glu-His-D-Phe-Arg-Trp-Gly-Lys-Pro-Val-NH₂ and analogs and homologs thereof.

The term "obesity" means the condition of excess body fat (adipose tissue), including by way of example in accordance with the National Institutes of Health Federal Obesity Clinical Guidelines for adults, whereby body mass index ("BMI") calculated by dividing body mass in kilograms by height in meters squared is equal to or greater than twenty-five (25), and further including an overweight condition and comparable obesity and overweight condition in children.

The term "prophylactically effective" or "preventive" means the amount of MC4r agonist and GLP-1 receptor agonist, including the ratio of MC4r agonist and GLP-1 receptor agonist, which will prevent or inhibit affliction or mitigate affliction of a mammal with a medical condition that a medical doctor or other clinician is trying to prevent, inhibit, or mitigate before a patient begins to suffer from the specified disease or disorder, including but not limited to obesity, diabetes or exacerbation of metabolic syndrome.

As used herein, the term "pharmacologically effective amount" (including "therapeutically effective amount") means an amount of the combination of MC4r agonist and GLP-1 receptor agonist, including the ratio of MC4r agonist and GLP-1 receptor agonist and/or the pharmacokinetic properties, including but not limited to half-life, according to the invention that is sufficient to induce a desired therapeutic or biological effect.

The term "sustained-release", as in a sustained-release form, sustained-release composition or sustained-release formulation, is intended to include a form of an active ingredient, or formulation for an active ingredient, which has an extended in vivo half-life or duration of action. A sustained-release form may result from modification of the active ingredient, such as modifications that extend circulation residence time, decrease rates of degradation, decrease rates of clearance or the like, or may result from formulations or compositions which provide for extended release of the active ingredient, such as use of various liposomes, emulsions, micelles, matrices and the like. A controlled-release form or formulation is a type of sustained-release form or formulation.

The terms "synergy", "synergism" or "synergistic" mean more than the expected additive effect of a combination. A synergistic effect may be attained when the active ingredients are: (a) co-formulated and administered or delivered simultaneously in a combined, unit dosage formulation; (b) delivered as separate formulations at either then same or different times; or (c) by some other regimen. A synergistic effect may be attained, by way of example, by daily administration of one active ingredient, such as with a half-life of two to six hours, and weekly or longer administration of another active ingredient, such as with a half-life of two or greater days.

A pharmaceutical composition is effective in "treatment of obesity" or "to induce weight loss" when the composition induces, over a period of time from 12 to 52 weeks, a statistically significant and placebo-adjusted decrease in body weight of at least about 5.0% in a cohort of subjects with a baseline mean BMI≥27 kg/m².

The term "therapeutically effective amount" means the amount of MC4r agonist and GLP-1 receptor agonist, including the ratio of MC4r agonist and GLP-1 receptor agonist, which will elicit a biological or medical response in the mammal that is being treated by a medical doctor or other clinician.

The terms "treat," "treating" and "treatment," as used herein, contemplate an action that occurs while a patient is suffering from, or at risk of suffering from, the specified disease or disorder, which reduces the onset, incidence or severity of the disease or disorder.

Obesity, Diabetes and Related Metabolic Syndrome.

The compositions and methods disclosed herein can be used for both medical applications and animal husbandry or veterinary applications. Typically, the methods are used in humans, but may also be used in other mammals. The term "patient" is intended to denote a mammalian individual, and is so used throughout the specification and in the claims. The primary applications of the present invention involve human patients, but the present invention may be applied to laboratory, farm, zoo, wildlife, pet, sport or other animals.

The combination of MC4r agonist and GLP-1 receptor agonist, including the ratio of MC4r agonist to GLP-1 receptor agonist and methods for the administration thereof, is believed to be useful in prophylaxis and treatment of diseases, disorders and/or conditions which are energy homeostasis and metabolism related (such as diabetes, in particular type 2 diabetes; dyslipidemia; fatty liver; hypercholesterolemia; hypertriglyceridemia; hyperuricacidemia; impaired glucose tolerance; impaired fasting glucose; insulin resistance syndrome; and metabolic syndrome), food intake related (such as hyperphagia; binge eating; bulimia; and compulsive eating) and/or energy balance and body weight related diseases, disorders and/or conditions, more particularly such diseases, disorders and conditions characterized by excess body weight and/or excess food intake.

In one aspect, it is believed that use of a sustained-release, controlled-release or long acting GLP-1 receptor agonist in combination with a periodically administered MC4r agonist is efficacious in treating obesity, diabetes and related metabolic syndrome. The sustained-release or controlled-release GLP-1 receptor agonist may be a GLP-1 receptor agonist that has a comparatively short circulation half-life but is continuously administered, such as by continuous infusion using a pump device. Alternatively the sustained-release or controlled-release GLP-1 receptor agonist may have a duration of action greater than about twenty-four hours, including, but are not limited to, liraglutide, long acting forms of exenatide, dulaglutide, taspoglutide and albiglutide. With GLP-1 receptor agonists with a duration of action greater than about twenty-four hours, the GLP-1 receptor agonists may be administered by subcutaneous injection on a daily, weekly, biweekly or other schedule. The MC4r agonist may have a duration of action less than twelve hours, preferably less than eight hours, and more preferably less than about six hours, such as a peptide with a plasma circulation half-life of less than about four hours, preferably less than about two hours. In this instance, the MC4r agonist can be administered by subcutaneous injection separately from the GLP-1 receptor agonist. In one particularly preferred embodiment, the MC4r agonist is administered prior to periods of high caloric consumption, such as prior to a meal, such as about one-half hour to two hours prior to breakfast, lunch, dinner or evening or other snacking periods. In this embodiment, only one daily injection of MC4r agonist may be required, or alternatively two daily injections may be administered.

The combination of MC4r agonist and GLP-1 receptor agonist, including the ratio of MC4r agonist and GLP-1 receptor agonist, the relative durations of action of each of the MC4r agonist and GLP-1 receptor agonist in combination with administration schedules, and methods for the administration thereof, are particularly believed to be useful for treatment of body weight related diseases, disorders and/or conditions characterized by excess body weight, including obesity and overweight (by promotion of weight loss, maintenance of weight loss, and/or prevention of weight gain, including medication-induced weight gain or weight gain subsequent to cessation of smoking), and diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro- and micro-vascular diseases; steatosis (e.g. in the liver); gall stones; and gallbladder disorders.

It will be understood that there are medically accepted definitions of obesity and overweight. A patient may be identified by, for example, measuring body mass index (BMI), which is calculated by dividing weight in kilograms by height in meters squared, and comparing the result with the definitions. The recommended classifications for BMI in humans, adopted by the Expert Panel on the Identification, Evaluation and Treatment of Overweight and Obesity in Adults, and endorsed by leading organizations of health professionals, are as follows: underweight <18.5 kg/m², normal weight 18.5-24.9 kg/m², overweight 25-29.9 kg/m₂, obesity (class 1) 30-34.9 kg/m², obesity (class 2) 35-39.9 kg/m², extreme obesity (class 3)≥40 kg/m² (Practical Guide to the Identification, Evaluation, and Treatment of Overweight and Obesity in Adults, The North American Association for the Study of Obesity (NAASO) and the National Heart, Lung and Blood Institute (NHLBI) 2000). Modifications of this classification may be used for specific ethnic groups. Another alternative for assessing overweight and obesity is by measuring waist circumference. There are several proposed classifications and differences in the cut-offs based on ethnic group. For instance, according to the classification from the International Diabetes Federation, men having waist circumferences above 94 cm (cut off for europids) and women having waist circumferences above 80 cm (cut off for europids) are at higher risk of diabetes, dyslipidemia, hypertension and cardiovascular diseases because of excess abdominal fat. Another classification is based on the recommendation from the Adult Treatment Panel III where the recommended cut-offs are 102 cm for men and 88 cm for women. However, the methods, combinations and compositions of the invention may also be used for reduction of self-diagnosed overweight and for decreasing the risk of becoming obese due to life style, genetic considerations, heredity and/or other factors.

Methods of Administration and Use.

The method of administration and use of the combination of MC4r agonist and GLP-1 receptor agonist, including the ratio of MC4r agonist and GLP-1 receptor agonist and methods for the administration thereof, varies depending upon the characteristics of the drug components utilized in the present invention, the disease, indication, condition or syndrome to be treated, and other factors known to those in the art. In general, any method of administration and use known in the art or hereafter developed may be employed in the present invention. Without limiting the foregoing, the following methods of administration and use have specific application for the indicated indications.

Compositions comprising the combination of MC4r agonist and GLP-1 receptor agonist, including the ratio of MC4r agonist and GLP-1 receptor agonist and methods for the administration thereof, utilized in the present invention may administered by any suitable means for therapy, including prophylactic therapy, of obesity, diabetes and/or metabolic syndrome. In one aspect, the composition is formulated for subcutaneous injection, and a subcutaneous injection is given one or more times each day, preferably prior to a period of high caloric intake, such as a meal, more preferably between about one and about three hours prior to a period of high caloric intake, such as a meal. In another aspect, the composition is formulated as an injectable controlled-release or sustained-release formulation. In one embodiment, the MC4r agonist and GLP-1 receptor agonist utilized in the present invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment the MC4r agonist and GLP-1 receptor agonist utilized in the present invention are formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining the MC4r agonist and GLP-1 receptor agonist utilized in the present invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a controlled-release or sustained-release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of peptide, the biodegradation rate of the polymer, and other factors known to those of skill in the art.

In another and preferred embodiment, different routes of administration are employed for the administration of each of the MC4r agonist and GLP-1 receptor agonist. Thus the GLP-1 receptor agonist and the MC4r agonist may each independently be administered by any known method, such as subcutaneous administration, intranasal administration, intravenous administration, intramuscular administration, oral administration, buccal administration, sublingual administration, transdermal administration or other means known in the art, but the method of administration may be different for the MC4r agonist and the GLP-1 receptor agonist.

In one aspect, the invention provides a composition comprising a MC4r agonist and a GLP-1 receptor agonist. The composition may have a synergistic anti-obesity effect. The composition may also include a sustained-release formulation. In the composition, at least one of the MC4r agonist and the GLP-1 receptor agonist may have, upon administration, a duration of action of at least twenty-four hours. Alternatively, in the composition both of the MC4r agonist and the GLP-1 receptor agonist have, upon administration, a duration of action of at least twenty-four hours.

In another aspect, the invention provides a method of treating a patient with obesity, comprising administering to the patient a combination of (a) a MC4r agonist and (b) a GLP-1 receptor agonist. In the method, at least one of the combination of (a) a MC4r agonist and (b) a GLP-1 receptor agonist is in a therapeutically effective amount with respect to treatment of obesity or inducing weight loss. Alternatively, in the method each of the (a) MC4r agonist and (b) GLP-1 receptor agonist are administered in an amount that is not effective with respect to treatment of obesity or inducing weight loss if administered alone. The combination may elicit a synergistic effect on treatment of obesity. Alternatively, if the compounds induce minimal weight loss the combination may elicit an additive effect on treatment of obesity. The method may further comprise a sustained-release formulation. In the method, at least one of the MC4r agonist and the GLP-1 receptor agonist may have, upon administration, a duration of action of at least twenty-four hours. Alternatively, in the method both of the MC4r agonist and the GLP-1 receptor agonist may have, upon administration, a duration of action of at least twenty-four hours.

In another aspect, the invention provides a composition comprising a combination of a MC4r agonist and a GLP-1 receptor agonist whereby such MC4r agonist and a GLP-1 receptor agonist are in such respective proportions as to decrease insulin levels at a selected time after administration as compared to insulin levels prior to initial administration of the composition. The decrease in insulin levels from baseline can be at least about ten percent, between about ten percent and about fifty percent, at least about twenty-five percent or at least about fifty percent. The decrease in insulin levels from baseline in a population administered the composition is greater than the decrease in insulin levels in a corresponding population administered either a MC4r agonist or a GLP-1 receptor agonist but not both, including where the corresponding population is administered the same quantity of either a MC4r agonist or a GLP-1 receptor agonist as is administered to the population receiving the composition. The composition may comprise a sustained-release formulation. At least one of the MC4r agonist and the GLP-1 receptor agonist in the composition may have, upon administration, a duration of action of at least twenty-four hours. Alternatively, both the MC4r agonist and the GLP-1 receptor agonist have, upon administration, a duration of action of at least twenty-four hours.

In another aspect, the invention provides a pharmaceutical combination comprising as components (a) a MC4r agonist, and (b) a GLP-1 receptor agonist; wherein components (a) and (b) are present in such weight or molar ratio that the composition exerts a synergistic effect upon administration to a patient. The pharmaceutical composition may comprise at least one pharmaceutically acceptable carrier. There is thus provided a pharmaceutical dosage form comprising a pharmaceutical combination as described and at least one pharmaceutically acceptable carrier. The dosage form may be suitable for oral, intravenous, intraarterial, intraperitoneal, intradermal, transdermal, intrathecal, intramuscular, intranasal, transmucosal, subcutaneous, or rectal administration. In the dosage form, at least one of the components (a) and (b) may be present in sustained-release form, or alternatively both of the components (a) and (b) may be present in sustained-release form. The dosage form may further comprise a sustained-release formulation. In the dosage form, at least one of the MC4r agonist and the GLP-1 receptor agonist may have, upon administration, a duration of action of at least twenty-four hours, or alternatively, both of the MC4r agonist and the GLP-1 receptor agonist may have, upon administration, a duration of action of at least twenty-four hours. The pharmaceutical combination may be utilized in a method of treating obesity, diabetes or metabolic syndrome in a mammal in need thereof, said method comprising administering to said mammal a pharmacologically effective amount of a pharmaceutical combination.

In another aspect, the invention provides a method of treating obesity, diabetes or metabolic syndrome in a mammal in need thereof, comprising separate administration to the patient of a MC4r agonist and a GLP-1 receptor agonist. In the method, the quantity and schedule of administration of the MC4r agonist and the GLP-1 receptor agonist may together be sufficient to produce synergistic effect, or alternatively additive effect, in the treatment of obesity, diabetes or metabolic syndrome. Alternatively, in the method the quantity and schedule of administration of the MC4r agonist and the GLP-1 receptor agonist may together be sufficient to initiate a desired pharmacological response in the treatment of obesity, diabetes or metabolic syndrome in the mammal. In the method, the desired pharmacological response may comprise a decrease in body weight, a decrease in body mass index, a decrease in glucose levels or a decrease in insulin levels, or a combination of the foregoing. In the practice of the method, the MC4r agonist and the GLP-1 receptor agonist may be administered simultaneously to the mammal, may be administered sequentially to the mammal in either order and may be administered via different pathways of administration. The MC4r agonist may be administered by subcutaneous bolus injection and the GLP-1 receptor agonist may be administered by continuous infusion. Continuous infusion of the GLP-1 receptor agonist may comprise implantation of an osmotic delivery device, subcutaneous infusion, or both. The subcutaneous bolus injection of the MC4r agonist may comprise subcutaneous injection no more than twice daily, or alternatively no more than once daily. The MC4r agonist may comprise a sustained-release form. Similarly, the GLP-1 receptor agonist that is administered may be a sustained-release GLP-1 receptor agonist, with a duration of action of at least about twenty-four hours, at least about one week or at least about two weeks. In one embodiment, where a sustained release GLP-1 receptor agonist is employed, the MC4r agonist is not sustained-release. In such embodiment, the MC4r agonist may be administered no more than about twice per day, or alternatively no more than once per day. In such embodiment, the MC4r agonist which is not sustained-release may have a plasma circulation half-life of less than about 6 hours, or alternatively of less than about 3 hours or less than about 2 hours. In another embodiment, the MC4r agonist is administered by intramuscular injection of a sustained-release form and the GLP-1 receptor agonist is administered by continuous infusion. Continuous infusion of the GLP-1 receptor agonist may comprise implantation of an osmotic delivery device.

In another aspect, there is provided a method of treating obesity, diabetes or metabolic syndrome in a patient, comprising bolus parenteral administration of a quantity of a MC4r agonist and infusion administration of a quantity of GLP-1 receptor agonist, wherein the quantity of MC4r agonist and the quantity of GLP-1 receptor agonist are together sufficient to initiate a desired pharmacological response in the treatment of obesity, diabetes or metabolic syndrome in the patient. In this method, the desired pharmacological response may comprise a decrease in body weight, a decrease in body mass index, a decrease in glucose levels or a decrease in insulin levels, or a combination of the foregoing. The quantity of MC4r agonist and the quantity of GLP-1 receptor agonist may together be sufficient to produce synergistic effect in the treatment of obesity, diabetes or metabolic syndrome in the patient. In another embodiment, the quantity of each of the MC4r agonist and the GLP-1 receptor agonist is not sufficient, if either is administered as monotherapy, to initiate the desired pharmacological response in the treatment of obesity, diabetes or metabolic syndrome in the patient. Alternatively, in the method the quantity of MC4r agonist administered may not be sufficient to initiate the desired pharmacological response in the treatment of obesity, diabetes or metabolic syndrome in the patient when administered as a monotherapy. Alternatively, the quantity of GLP-1 receptor agonist administered may not be sufficient to initiate the desired pharmacological response in the treatment of obesity, diabetes or metabolic syndrome in the patient when administered as a monotherapy. In the method, the bolus parenteral administration of a quantity of a MC4r agonist may comprise subcutaneous administration. The quantity of a MC4r agonist may comprise a sustained-release form, or alternatively does not comprise a sustained-release form. Subcutaneous administration of the quantity of a MC4r agonist is no more than two times per day, or alternatively no more than one time per day. In the event of subcutaneous administration of a quantity of a MC4r agonist, the sustained-release form is administered no more than one time per day, or alternatively between about once per day and once per fifteen days or once per five days and once per ten days. Infusion administration of a quantity of GLP-1 receptor agonist may comprise implantation of an osmotic delivery device. In one embodiment, the combination of bolus parenteral administration of the quantity of a MC4r agonist and infusion administration of the quantity of GLP-1 receptor agonist elicits a synergistic effect on treatment of obesity, diabetes or metabolic syndrome in the patient, or alternatively elicits an additive effect on treatment of obesity, diabetes or metabolic syndrome in the patient.

In another aspect, the invention provides a method of decreasing side effects associated with therapeutic agents for treatment of glycemic control, obesity, diabetes or metabolic syndrome in a patient, comprising administration of a quantity of MC4r agonist, wherein the quantity of MC4r agonist administered is not sufficient to initiate the desired pharmacological response in treating at least one condition from the group comprising glycemic, obesity, diabetes and metabolic syndrome in the patient when administered as a monotherapy, and administration of a quantity of GLP-1 receptor agonist, wherein the quantity of GLP-1 receptor agonist administered is not sufficient to initiate the desired pharmacological response in treating at least one condition from the group comprising glycemic control, obesity, diabetes and metabolic syndrome in the patient when administered as a monotherapy, and wherein the quantity of the MC4r agonist and the quantity of GLP-1 receptor agonist are together effective to initiate the desired pharmacological response treating at least one condition from the group comprising glycemic control, obesity, diabetes and metabolic syndrome in the patient, thereby reducing side effects in the treatment of at least one of glycemic control, obesity, diabetes or metabolic syndrome in the patient. By way of example only, a patient that cannot tolerate doses of a GLP-1 receptor agonist sufficient to achieve the desired glycemic control may, through the use of a tolerable but ineffective dose of a GLP-1 receptor agonist in combination with an MC4r agonist not sufficient, if used alone, to achieve the desired glycemic control, obtain the desired glycemic control.

In another aspect, the invention provides a method of treating obesity, diabetes or metabolic syndrome in a patient either not responsive to or marginally responsive to a GLP-1 receptor agonist, comprising the steps of establishing a dose of a GLP-1 receptor agonist at which the patient has a marginal rate of responsiveness with respect to treating obesity, diabetes or metabolic syndrome with the GLP-1 receptor agonist, administration of the marginally responsive dose of the GLP-1 receptor agonist, and administration of a MC4r agonist, wherein the dose of the GLP-1 receptor agonist and the quantity of MC4r agonist are effective to increase responsiveness with respect to treating obesity, diabetes or metabolic syndrome. In such method, administration of the marginally responsive dose of the GLP-1 receptor agonist may comprise continuous infusion. In such method, administration of the MC4r agonist may comprise bolus parenteral administration, including subcutaneous administration. Administration of the MC4r agonist may alternatively comprise a sustained-release form, including intramuscular injection of a sustained-release form. In one embodiment of the method, the combination may elicit a synergistic effect on treatment of obesity, or alternatively may elicit an additive effect on treatment of obesity. In another embodiment of the method, the GLP-1 receptor agonist administered is a sustained-release GLP-1 receptor agonist, optionally with a duration of action of at least about twenty-four hours, or alternatively of at least about one week or at least about two weeks. In the practice of the method, in one embodiment the MC4r agonist is not sustained-release, and is administered no more than about twice per day, or alternatively no more than once per day. The MC4r agonist which is not sustained-release may have a plasma circulation half-life of less than about 6 hours, or less than about 3 hours, or less than about 2 hours.

Salt Form(s) of MC4r Monist and GLP-1 Receptor Agonist Utilized in the Present Invention.

The MC4r agonist and GLP-1 receptor agonist utilized in the present invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the MC4r agonist and GLP-1 receptor agonist utilized in the present invention are basic, acid addition salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of MC4r agonist and GLP-1 receptor agonist utilized in the present invention can be prepared in a suitable solvent for the peptide and an excess of an acid, such as hydrochloric, hydrobromic, sulfuric, phosphoric, acetic, trifluoroacetic, citric, tartaric, maleic, succinic or methanesulfonic acid. The acetate and trifluoroacetic acid salt forms are especially useful. Where MC4r agonist or GLP-1 receptor agonist utilized in the present invention include an acidic moiety, suitable pharmaceutically acceptable salts may include alkali metal salts, such as sodium or potassium salts, or alkaline earth metal salts, such as calcium or magnesium salts. It is also to be understood that certain peptides can exist in solvated forms, including solvates of the free peptide or solvates of a salt of the compound, as well as unsolvated forms. The term "solvate" is used herein to describe a molecular complex comprising one or more compounds utilized in the invention and one or more pharmaceutically acceptable solvent molecules, for example, ethanol. The term "hydrate" is employed when said solvent is water. It is to be understood that all polymorphs, including mixtures of different polymorphs, are included within the scope of the peptides utilized in the invention.

Pharmaceutical Compositions.

In one aspect, the invention provides a pharmaceutical composition that includes an MC4r peptide and a GLP-1 receptor agonist peptide utilized in the present invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Depending on the desired route of administration, and whether the MC4r agonist and GLP-1 receptor agonist are formulated together or formulated separately, the formulation(s) of a composition including at least one of the MC4r agonist and GLP-1 receptor agonist utilized in the present invention may be varied. Thus the formulation may be suitable for subcutaneous injection, intravenous injection, topical applications, ocular applications, nasal spray applications, inhalation applications, other transdermal applications and the like.

The MC4r and GLP-1 peptide compositions utilized in the present invention may be formulated or compounded into pharmaceutical compositions that include at least one MC4r agonist peptide and at least one GLP-1 receptor agonist peptide together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxyl propyl cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, cellulose derivatives, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, controlled-release, slow-release or sustained-release formulations and additives may be employed, so that the dosage may be formulated so as to provide delivery of an MC4r agonist peptide and GLP-1 receptor agonist peptide utilized in the present invention over a period of time.

In general, the actual quantity of MC4r agonist peptide and GLP-1 receptor agonist peptide utilized in the present invention administered to a patient will vary between fairly wide ranges depending on the mode of administration, the formulation used, and the response desired.

In practical use, the peptides of the invention as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like.

MC4r agonist peptides and GLP-1 receptor agonist peptides may be administered parenterally. Solutions or suspensions of these active peptides can be prepared in water suitably mixed with a surfactant such as hydroxy-propyl-cellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The MC4r agonist peptides and GLP-1 receptor agonist peptides utilized in the present invention may be therapeutically applied by means of nasal administration. By "nasal administration" is meant any form of intranasal administration of any of the peptides utilized in the present invention. The peptides may be in an aqueous solution, such as a solution including saline, citrate or other common excipients or preservatives. The peptides may also be in a dry or powder formulation.

The MC4r agonist peptides and GLP-1 receptor agonist peptides in the present invention may be formulated with any of a variety of agents that increase effective nasal absorption of drugs, including peptide drugs. These agents may increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the peptides comprising the formulation may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

The MC4r peptides utilized in the present invention may be therapeutically administered by means of an injection of a controlled-release or sustained-release formulation. In one embodiment, an MC4r agonist peptide utilized in the present invention is formulated for a deep intramuscular injection, such as in the gluteal or deltoid muscle, of a formulation with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment an MC4r agonist peptide utilized in the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable and bioerodible polymers, which are preferably also adhesive polymers, may be employed in a controlled-release or sustained-release injectable formulation. Alternatively other controlled-release or sustained-release formulations may be employed, including formulations permitting subcutaneous injection, which other formulations may include one or more of nano/microspheres (such as compositions including PLGA polymers), liposomes, emulsions (such as water-in-oil emulsions), gels, insoluble salts or suspensions in oil. The formulation may be such that an injection is required on a daily, weekly, monthly or other periodic basis, depending on the concentration and amount of cyclic peptide, the controlled- or sustained-release rate of the materials employed, and other factors known to those of skill in the art.

Particularly preferred are GLP-1 receptor agonist peptides which are long-acting, such as those GLP-1 receptor agonist peptides with a duration of action greater than about twenty-four hours. Representative examples of such GLP-1 receptor agonist peptides with a duration of action greater than about twenty-four hours include, but are not limited to, liraglutide, long acting forms of exenatide, dulaglutide, taspoglutide and albiglutide.

The GLP-1 receptor agonist peptides utilized in the present invention may be therapeutically administered by means of an injection of a controlled-release or sustained-release formulation. In one embodiment, a GLP-1 receptor agonist utilized in the present invention is formulated for a deep intramuscular injection, such as in the gluteal or deltoid muscle, of a formulation with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a GLP-1 receptor agonist utilized in the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable and bioerodible polymers, which are preferably also adhesive polymers, may be employed in a controlled-release or sustained-release injectable formulation. Alternatively other controlled-release or sustained-release formulations may be employed, including formulations permitting subcutaneous injection, which other formulations may include one or more of nano/microspheres (such as compositions including PLGA polymers), liposomes, emulsions (such as water-in-oil emulsions), gels, insoluble salts or suspensions in oil. The formulation may be such that an injection is required on a daily, weekly, monthly or other periodic basis, depending on the concentration and amount of cyclic peptide, the controlled- or sustained-release rate of the materials employed, and other factors known to those of skill in the art.

Routes of Administration.

If a composition including one or more MC4r agonist peptides utilized in the present invention is administered by injection, the injection may be intravenous, subcutaneous, intramuscular, intraperitoneal or other means known in the art. The MC4r agonist peptides utilized in the present invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

In one aspect the GLP-1 receptor agonist is a long acting form of GLP-1 receptor agonist, such as form of GLP-1 with an extended half-life or reduced clearance rate, or a controlled-release or sustained-release formulation. In a preferred embodiment, the GLP-1 receptor agonist has a duration of action greater than about twenty-four hours, including liraglutide and long acting forms of exenatide, dulaglutide, taspoglutide and albiglutide. Particularly preferred are GLP-1 receptor agonists which are not required to be administered more frequently than about once per day, once per week, once per every two weeks or one per month. Alternatively, the GLP-1 receptor agonist may have a short half-life, but may be continuously or intermittently administered, such as by means of an infusion device or depot formulation that allows slow release and gradual absorption.

For sustained-released forms of formulations of GLP-1 receptor agonist, in one embodiment a continuous delivery method and/or device may be employed. Such methods or devices may include intravenous infusion, which may be by gravity (such as using a collapsible plastic bag) or by an infusion pump. A variety of implantable devices and/or methods for continuous delivery are known, including but not limited to use of implantable devices (which may deliver active ingredient intravenously or subcutaneously). One type of implantable device that may be employed is an osmotic delivery device, such as that disclosed in U.S. Pat. No. 8,298,561.

Regardless of the formulation or route of administration employed for administration of GLP-1 receptor agonist, the MC4r agonist may be administered separately, and in a preferred embodiment is administered separately. Such separate administration may be, for example, by subcutaneous injection or transdermal administration. Intermittent delivery devices, including implantable intermittent delivery devices, may also be employed, which deliver, for example, a bolus quantity of MC4r agonist on a determined or variable schedule, such as once daily, twice daily or in conjunction with one or more periods of high caloric intake.

Therapeutically Effective Amount.

In general, the actual quantity of MC4r agonist and GLP-1 receptor agonist utilized in the present invention administered to a patient will vary between fairly wide ranges depending upon the mode of administration, characteristics of each of the MC4r agonist and GLP-1 receptor agonist, including pharmacokinetics and pharmacodynamics, the formulation used, and the response desired. The dosage for treatment is administration, by any of the foregoing means or any other means known in the art, of an amount sufficient to bring about the desired therapeutic effect. Thus a therapeutically effective amount includes an amount of MC4r agonist and an amount, which may be separately administered of GLP-1 receptor agonist. Preferably the therapeutically effective amount of MC4r agonist and GLP-1 receptor agonist results in measures of one or more parameters, such as insulin levels, blood glucose levels or other metabolic parameters, that are clinically superior to the measures of the same parameters obtained with MC4r agonist administered without administration of GLP-1 receptor agonist, or alternatively measures of the same parameters obtained with GLP-1 receptor agonist administered without the administration of MC4r agonist. Further preferably the therapeutic effective amount of MC4r agonist and GLP-1 receptor agonist results in a synergistic effect in the treatment of obesity, diabetes or metabolic syndrome, and specifically in at least one of inducing weight loss or inducing glycemic control.

In one aspect, a therapeutically effective amount is determined, in part, by selection of a dose of MC4r agonist and GLP-1 receptor agonist such that side effects are limited with respect to each of the MC4r agonist and GLP-1 receptor agonist. For example, a patient may be able to achieve desired glycemic control with a dose of GLP-1 receptor agonist which nonetheless induces undesired side effects, such as gastrointestinal symptoms or adverse reactions such as nausea, diarrhea, vomiting, constipation or the like. A lower dose of GLP-1 receptor agonist may not achieve desired glycemic control in the patient. However, the combination of the lower dose of GLP-1 receptor agonist together with a dose of MC4r agonist, which dose of MC4r agonist may not be sufficient to induce weight loss, are together sufficient to achieve the desired glycemic control without inducing undesired side effects, or inducing only reduced or tolerable side effects.

GLP-1 Receptor Agonists Utilized in the Present Invention.

Preferred GLP-1 receptor agonists with utility in the current invention include exenatide, liraglutide, lixisenatide, albiglutide, and dulaglutide, all of which are approved pharmaceutical drugs in the United States or elsewhere in the world. Other naturally expressed peptides which bind to the GLP-1 receptor may be employed in the invention, and are to be considered for purposes of this invention as GLP-1 receptor agonists, including pre-proglucagon, glucagon, GLP-1, GLP-2 and OXM. Other peptides and derivatives and modifications of peptides which may be employed in the current invention include, but are not limited to, those peptides and other compounds disclosed in WO2006/134340, WO2007/100535, WO2008/10101, WO2008/152403, WO2009/155257, WO2009/155258, WO2010/070252, WO2010/070253, WO2010/070255, WO2010/070251, WO2011/006497, WO2011/160630, WO2011/160633, WO2013/092703, WO2014/041195, WO2015/055802, WO2015149627, WO2015/155139, WO2015/155140, WO2015/155141, WO2015/155151, WO2015/193378, WO2015/193381, WO2016/0154014, and WO2016/046753.

MC4r Peptides Utilized in the Present Invention.

Preferred MC4r agonist peptides with utility in the current invention include the peptides disclosed in U.S. patent application Ser. No. 13/311,824, entitled "Melanocortin Receptor-Specific Peptides", filed Jul. 11, 2014, and issued as U.S. Pat. No. 8,846,601 on Sep. 30, 2014; U.S. patent application Ser. No. 14/328,995, entitled "Melanocortin Receptor-Specific Heptapeptides", filed Dec. 6, 2011, and issued as U.S. Pat. No. 8,846,601 on Sep. 30, 2014; International Application No. PCT/US2010/037589, published as International Publication No. WO 2010/144344, entitled "Melanocortin Receptor-Specific Peptides", filed on Jun. 7, 2010; and U.S. patent application Ser. No. 12/952,238, entitled "Melanocortin Receptor-Specific Peptides for Treatment of Sexual Dysfunction", filed on Nov. 23, 2010 and issued as U.S. Pat. No. 8,487,073 on Jul. 16, 2013.

In one aspect, the invention provides a cyclic heptapeptide which contains a core sequence derived from His-Phe-Arg-Trp (SEQ ID NO:3) within the cyclic portion, and where the amino acid in the first position is outside the cyclic portion and has a side chain including at least one primary amine, guanidine or urea group. Representative amino acids which may be in the first position include, but are not limited to, Dap, Dab, Orn, Lys, Cit or Arg.

The core sequence derived from His-Phe-Arg-Trp will include unsubstituted D-Phe, D-Nal 1 or D-Nal 2 in the Phe position, but typically a variety of amino acids may be utilized for the remaining amino acids in the core sequence. In general, the His position may be a substituted or unsubstituted Pro, or may be an amino acid with a side chain including at least one primary amine, secondary amine, alkyl, cycloalkyl, cycloheteroalkyl, aryl, heteroaryl, alcohol, ether, sulfide, sulfone, sulfoxide, carbomyl or carboxyl. The Arg position may be a substituted or unsubstituted Pro, or may be an amino acid with a side chain including at least one primary amine, secondary amine, guanidine, urea, alkyl, cycloalkyl, cycloheteroalkyl, aryl, heteroaryl, or ether. The Trp position may be an amino acid with a side chain including at least one substituted or unsubstituted aryl or heteroaryl.

Lactam-bridges are preferred for making the peptide cyclic, but other bridging groups are possible and contemplated, including specifically the groups:

—(CH$_2$)$_x$—C(=O)—NH—(CH$_2$)$_y$—,
—(CH$_2$)$_x$—NH—C(=O)—(CH$_2$)$_y$—,
—(CH$_2$)$_x$—S—S—(CH$_2$)$_y$—,
—(CH$_2$)$_x$—C(=O)—(CH$_2$)$_z$—C(=O)—(CH$_2$)$_y$—,
—(CH$_2$)$_x$—C(=O)—NH—C(=O)—(CH$_2$)$_y$—, or
—(CH$_2$)$_x$—NH—C(=O)—NH—(CH$_2$)$_y$—;

where x and y are each independently 1 to 5. For certain indications and uses, including without limitation for peptides more selective for MC4r than for MC1r or, in general, for other melanocortin receptors, particularly preferred are the bridging groups —(CH$_2$)$_2$—C(=O)—NH—(CH$_2$)$_3$— and —(CH$_2$)$_2$—NH—C(=O)—(CH$_2$)$_2$—. In this context, the teachings of U.S. patent application Ser. No. 13/311,817, filed on Dec. 6, 2011, entitled "Lactam-Bridged Melanocortin Receptor-Specific Peptides", and International Application No. PCT/US2010/037584, filed on Jun. 7, 2010 and published under the same title as International Publication No. WO 2010/144341, are incorporated herein by reference as if set forth in full.

The MC4r agonist peptides may contain one or more asymmetric elements such as stereogenic centers, stereogenic axes and the like, so that the peptides can exist in different stereoisomeric forms. For both specific and generically described peptides all forms of isomers at all chiral or other isomeric centers, including enantiomers and diastereomers, are intended to be covered herein. The peptides may each include multiple chiral centers, and may be used as a diastereomeric mixture or an enantiomerically enriched mixture, in addition to use of the peptides of the invention in enantiopure preparations. Typically, the peptides will be synthesized with the use of chirally pure reagents, such as specified L- or D-amino acids, using reagents, conditions and methods such that enantiomeric purity is maintained, but it is possible and contemplated that diastereomeric mixtures may be made. Such racemic mixtures may optionally be separated using well-known techniques and an individual enantiomer may be used alone. In cases and under specific conditions of temperature, solvents and pH wherein peptides may exist in tautomeric forms, each tautomeric form is contemplated as being included within this invention whether existing in equilibrium or predominantly in one form. Thus a single enantiomer of a peptide, which is an optically active form, can be obtained by asymmetric synthesis, synthesis from optically pure precursors, or by resolution of the racemates.

The invention is further intended to include prodrugs of the present peptides, which on administration undergo chemical conversion by metabolic processes before becoming active pharmacological peptides. In general, such prodrugs will be functional derivatives of the present peptides, which are readily convertible in vivo into an MC4r peptide. Prodrugs are any covalently bonded compounds, which release the active parent peptide drug in vivo. Conventional procedures for the selection and preparation of suitable prodrug derivatives are described, for example, in *Design of Prodrugs*, ed. H. Bundgaard, Elsevier, 1985. Typical examples of prodrugs have biologically labile protecting groups on a functional moiety, such as for example by esterification of hydroxyl, carboxyl or amino functions. Thus by way of example and not limitation, a prodrug includes peptides wherein an ester prodrug form is employed, such as, for example, lower alkyl esters of an R group of the peptide, such as where R is —OH, which lower alkyl esters may include from 1-8 carbons in an alkyl radical or aralkyl esters which have 6-12 carbons in an aralkyl radical. Broadly speaking, prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce an active parent peptide drug in vivo.

The subject invention also includes peptides in which one or more atoms are replaced by an atom having an atomic mass or mass number different from the atomic mass or mass number usually found in nature. Examples of isotopes that can be incorporated into compounds of the invention include isotopes of hydrogen, carbon, nitrogen and oxygen, such as $^2$H, $^3$H, $^{13}$C, $^{14}$C, $^{15}$N, $^{18}$O, $^{17}$O, and respectively. MC4r agonist peptides utilized in the present invention and pharmaceutically acceptable salts or solvates which contain the aforementioned isotopes and/or other isotopes of other atoms are within the scope of this invention. Certain isotopically-labeled compounds, for example those into which radioactive isotopes such as $^3$H and $^{14}$C are incorporated, may have use in a variety of assays, such as in drug and/or substrate tissue distribution assays. Substitution with heavier isotopes, such as substitution of one or more hydrogen atoms with deuterium ($^2$H), can provide pharmacological advantages in some instances, including increased metabolic stability. Isotopically labeled peptides can generally be prepared by substituting an isotopically labeled reagent for a non-isotopically labeled reagent.

Tests and Assays Employed in Evaluation of MC4r Peptides of the Present Invention.

The MC4r agonist peptides may be tested by a variety of assay systems and animal models to determine binding, functional status and efficacy.

A competitive inhibition binding assay may be performed using membrane homogenates prepared from HEK-293 cells that express recombinant hMC4r, hMC3r, or hMC5r, and from B-16 mouse melanoma cells (containing endogenous MC1r). In some instances, HEK-293 cells that express recombinant hMC1r are employed. In the examples that follow, all MC3r, MC4r and MC5r values are for human recombinant receptors. MC1r values are for B-16 mouse melanoma cells, unless the heading is "hMC1 r", in which case the value is for human recombinant MC1r. Assays were performed in 96 well GF/B Millipore multiscreen filtration plates (MAFB NOB10) pre-coated with 0.5% bovine serum albumin (Fraction V). Membrane homogenates were incubated with 0.2 nM (for hMC4r) 0.4 nM (for MC3r and MC5r) or 0.1 nM (for mouse B16 MC1r or hMC1r) [$I^{125}$]-NDP-α-MSH (Perkin Elmer) and increasing concentrations of test peptides of the present invention in buffer containing 25 mM HEPES buffer (pH 7.5) with 100 mM NaCl, 2 mM CaCl$_2$, 2 mM MgCl$_2$, 0.3 mM 1,10-phenanthroline, and 0.2% bovine serum albumin. After incubation for 60 minutes at 37° C., the assay mixture was filtered and the membranes washed three times with ice-cold buffer. Filters were dried and counted in a gamma counter for bound radioactivity. Non-specific binding was measured by inhibition of binding of [$I^{125}$]-NDP-α-MSH in the presence of 1 μM NDP-α-MSH. Maximal specific binding (100%) was defined as the difference in radioactivity (cpm) bound to cell membranes in the absence and presence of 1 μM NDP-α-MSH. Radioactivity (cpm) obtained in the presence of test compounds was normalized with respect to 100% specific binding to determine the percent inhibition of [$I^{125}$]-NDP-α-MSH binding. Each assay was conducted in triplicate and the actual mean values are described, with results less than 0% reported as 0%. Ki values for test peptides of the present invention were determined using Graph-Pad Prism® curve-fitting software.

Alternatively, a competitive inhibition binding assay may be performed employing Eu-NDP-α-MSH (PerkinElmer Life Sciences catalog No. AD0225) with determination by time-resolved fluorometry (TRF) of the lanthanide chelate. In comparison studies with [$I^{125}$]-NDP-α-MSH, the same values, within experimental error ranges, were obtained for percent inhibition and Ki. Typically competition experiments to determine Ki values were conducted by incubating membrane homogenates prepared from HEK-293 cells that express recombinant hMC4r with 9 different concentrations of test compounds of interest and 2 nM of Eu-NDP-α-MSH in a solution containing 25 mM HEPES buffer with 100 mM NaCl, 2 mM CaCl$_2$, 2 mM MgCl$_2$ and 0.3 mM 1,10-phenanthroline. After incubation for 90 minutes at 37° C., the reaction was stopped by filtration over AcroWell 96-well filter plates (Pall Life Sciences). The filter plates were washed 4 times with 200 μL of ice-cold phosphate-buffered saline. DELFIA Enhancement solution (PerkinElmer Life Sciences) was added to each well. The plates were incubated on a shaker for 15 minutes and read at 340 nm excitation and 615 nm emission wavelengths. Each assay was conducted in duplicate and mean values were utilized. Ki values were determined by curve-fitting with Graph-Pad Prism® software using a one-site fixed-slope competition binding model.

Competitive binding studies using [$I^{125}$]-AgRP (83-132) can be conducted using membrane homogenates isolated from cells that express hMC4r. The assays were performed in 96-well GF/B Millipore multiscreen filtration plates (MAFB NOB10) pre-coated with 0.5% bovine serum albumin (Fraction V). The assay mixture contained 25 mM HEPES buffer (pH 7.5) with 100 mM NaCl, 2 mM CaCl$_2$, 2 mM MgCl$_2$, 0.3 mM 1,10-phenanthroline, 0.5% bovine serum albumin, membrane homogenates, radioligand [$I^{125}$]-AgRP (83-132) (Perkin Elmer) and increasing concentrations of peptides of the present invention in a total volume of 200 μL. Binding was measured at radioligand concentrations of 0.2 nM. After incubating for 1 hour at 37° C., the reaction mixture was filtered and washed with assay buffer containing 500 mM NaCl. The dried discs were punched out from the plate and counted on a gamma counter. Ki values for test peptides of the present invention were determined using Graph-Pad Prism® curve-fitting software.

Accumulation of intracellular cAMP was examined as a measure of the ability of the MC4r peptides to elicit a functional response in HEK-293 cells that express MC4r. Confluent HEK-293 cells that express recombinant hMC4r were detached from culture plates by incubation in enzyme-free cell dissociation buffer. Dispersed cells were suspended in Earle's Balanced Salt Solution containing 10 mM HEPES (pH 7.5), 1 mM MgCl$_2$, 1 mM glutamine, 0.5% albumin and 0.3 mM 3-isobutyl-1-methyl-xanthine (IBMX), a phosphodiesterase inhibitor. The cells were plated in 96-well plates at a density of $0.5 \times 10^5$ cells per well and pre-incubated for 10 minutes. Cells were exposed for 15 minutes at 37° C. to peptides of the present invention dissolved in DMSO (final DMSO concentration of 1%) at a concentration range of 0.05-5000 nM in a total assay volume of 200 μL. NDP-α-MSH was used as the reference agonist. cAMP levels were determined by an HTRF® cAMP cell-based assay system from Cisbio Bioassays utilizing cryptate-labeled anti-cAMP and d2-labeled cAMP, with plates read on a Perkin-Elmer Victor plate reader at 665 and 620 nM. Data analysis was performed by nonlinear regression analysis with Graph-Pad Prism® software. The maximum efficacies of the test peptides of the present invention were compared to that achieved by the reference melanocortin agonist NDP-α-MSH.

Food Intake and Body Weight Change.

Change in food intake and body weight can be evaluated using animal models. Male Sprague-Dawley rats are obtained from Hilltop Lab Animals, Inc. (Scottsdale, Pa.) or other vendors. Animals are individually housed in conventional polystyrene hanging cages and maintained on a controlled 12 hour on/off light cycle. Water and pelleted food is provided ad libitum. The rats are dosed IV with vehicle or selected peptides (0.3 to 1.0 mg/kg), or dosed subcutaneously with vehicle or selected peptides (doses up to 30 mg/kg). The changes in body weight and food intake for the 24 hour period after dosing is determined. The changes in body weight and food intake for the 48 hour and 72 hour periods after dosing can also be measured to determine reversal of changes in body weight and food intake effects back to baseline levels.

Combination with Third Agent for Certain Indications.

The combination of MC4r agonist and GLP-1 receptor agonist, including the ratio of MC4r agonist and GLP-1 receptor agonist and/or pharmacokinetic properties, including the half-life of MC4r agonist and GLP-1 receptor agonist, and methods for the administration thereof, compositions and methods of the present invention may be used for treatment of any of the foregoing diseases, indications, conditions or syndromes in combination with a third additional other pharmaceutically active compound. Such combination administration may be by means of a single dosage form which includes both the combination of MC4r agonist and GLP-1 receptor agonist, including the ratio of MC4r agonist and GLP-1 receptor agonist and methods for the administration thereof, of the present invention and one more other pharmaceutically active compounds, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. Without meaning to limit combination therapies, the following exemplifies certain combination therapies which may be employed.

In particular other anti-obesity drugs that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or gastrointestinal motility may be employed. Drugs that reduce energy intake include, in part, various pharmacological agents, referred to as anorectic drugs, which are used as adjuncts to behavioral therapy in weight reduction programs.

Generally, a total dosage of the below-described obesity control agents or medications, when used in combination with one or more peptides of the present invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

The combination of MC4r agonist and GLP-1 receptor agonist, including the ratio of MC4r agonist and GLP-1 receptor agonist and methods for the administration thereof, of the invention may in addition or alternatively further be combined with one or more other pharmacologically active agent(s) that is (are) useful in the treatment of diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

According to a further aspect of the invention there is provided a combination treatment comprising the administration of a pharmacologically effective amount of the combination of MC4r agonist and GLP-1 receptor agonist, including the ratio of MC4r agonist and GLP-1 receptor agonist and methods for the administration thereof, according to the invention, optionally together with one or more pharmaceutically acceptable diluents or carriers, with the simultaneous, sequential or separate administration one or more of the following agents selected from:

insulin and insulin analogues;

insulin secretagogues, including sulphonylureas (e.g. glipizide) and prandial glucose regulators (sometimes called "short-acting secretagogues"), such as meglitinides (e.g. repaglinide and nateglinide);

agents that improve incretin action, for example dipeptidyl peptidase IV (DPP-4) inhibitors (e.g. vildagliptin, saxagliptin, and sitagliptin);

insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity;

agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators;

agents designed to reduce/slow the absorption of glucose from the intestine, such as alpha-glucosidase inhibitors (e.g. miglitol and acarbose);

agents which antagonise the actions of or reduce secretion of glucagon, such as amylin analogues (e.g. pramlintide);

agents that prevent the reabsorption of glucose by the kidney, such as sodium-dependent glucose transporter 2 (SGLT-2) inhibitors (e.g. dapagliflozin);

agents designed to treat the complications of prolonged hyperglycaemia, such as aldose reductase inhibitors (e.g. epalrestat and ranirestat); and agents used to treat complications related to micro-angiopathies;

anti-dyslipidemia agents, such as HMG-CoA reductase inhibitors (statins, e.g. rosuvastatin) and other cholesterol-lowering agents; PPARα agonists (fibrates, e.g. gemfibrozil and fenofibrate); bile acid sequestrants (e.g. cholestyramine); cholesterol absorption inhibitors (e.g. plant sterols (i.e. phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof; anti-oxidants, such as probucol; and omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem); angiotensin II receptor antagonists (e.g. candesartan); aldosterone receptor antagonists (e.g. eplerenone); centrally acting adrenergic drugs, such as central alpha agonists (e.g. clonidine); and diuretic agents (e.g. furosemide);

haemostasis modulators, including antithrombotics, such as activators of fibrinolysis; thrombin antagonists; factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole);

anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant);

feeding behavior modifying agents, such as orexin receptor modulators and melanin-concentrating hormone (MCH) modulators;

neuropeptide Y (NPY)/NPY receptor modulators;

pyruvate dehydrogenase kinase (PDK) modulators;

serotonin receptor modulators;

leptin/leptin receptor modulators;

ghrelin/ghrelin receptor modulators; or monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt, solvate, solvate of such a salt or a prodrug thereof, optionally together with a pharmaceutically acceptable carrier to a mammal, such as man, in need of such therapeutic treatment.

Examples

The invention is further exemplified by the following non-limiting examples:

1. The following MC4r agonist peptides were synthesized and averaged MC4r Ki values for peptides were determined as indicated. All Ki values were determined using [$I^{125}$]-NDP-α-MSH unless marked with an "*", in which event the values were determined using Eu-NDP-α-MSH. Ki values marked "ND" were not determined.

| No. | Amino Acid Sequence | MC4r Ki (nM) |
|---|---|---|
| 1 | Ac-Arg-cyclo(Asp-His-D-Phe-Arg-Trp-Lys)-NH$_2$ | 5 |
| 2 | Ac-Arg-cyclo(Asp-Lys-D-Phe-Arg-Trp-Lys)-NH$_2$ | 30 |
| 3 | Ac-Arg-cyclo(Asp-Ser-D-Phe-Arg-Trp-Lys)-NH$_2$ | 172 |
| 4 | Ac-Arg-cyclo(Asp-Ser-D-Phe-Lys-Trp-Lys)-NH$_2$ | 4293 |
| 5 | Ac-Arg-cyclo(Asp-Ala-D-Phe-Cit-Trp-Lys)-NH$_2$ | 2048* |
| 6 | Ac-Arg-cyclo(Asp-His-D-Phe-Lys-Trp-Lys)-NH$_2$ | 533* |
| 7 | Ac-Arg-cyclo(Asp-Lys-D-Phe-Lys-Trp-Lys)-NH$_2$ | 2957* |
| 8 | Ac-Arg-cyclo(Asp-Ala-D-Phe-Lys-Trp-Lys)-NH$_2$ | 3018* |
| 9 | Ac-Arg-cyclo(Asp-Ala-D-Phe-Arg-Trp-Lys)-NH$_2$ | 19* |
| 10 | Ac-Arg-cyclo(Asp-Phe-D-Phe-Arg-Trp-Lys)-NH$_2$ | 51* |
| 11 | Ac-Arg-cyclo(Asp-Tyr-D-Phe-Arg-Trp-Lys)-NH$_2$ | 43* |
| 12 | Ac-Arg-cyclo(Asp-Leu-D-Phe-Arg-Trp-Lys)-NH$_2$ | 33* |
| 13 | Ac-Arg-cyclo(Asp-Nle-D-Phe-Arg-Trp-Lys)-NH$_2$ | 30* |
| 14 | Ac-Arg-cyclo(Asp-Thr(Bzl)-D-Phe-Arg-Trp-Lys)-NH$_2$ | 1 |
| 15 | Ac-Arg-cyclo(Asp-Hyp(Bzl)-D-Phe-Arg-Trp-Lys)-NH$_2$ | 0.7* |
| 16 | Ac-Arg-cyclo(Asp-Val-D-Phe-Arg-Trp-Lys)-NH$_2$ | 23 |
| 17 | Ac-Arg-cyclo(Asp-Aic-D-Phe-Arg-Trp-Lys)-NH$_2$ | ND |
| 18 | Ac-Arg-cyclo(Asp-Pro(4R-Bzl)-D-Phe-Arg-Trp-Lys)-NH$_2$ | 3* |
| 19 | Ac-Arg-cyclo(Asp-His-D-Nal 1-Arg-Trp-Lys)-NH$_2$ | 3 |
| 20 | Ac-Arg-cyclo(Asp-D-Nle-D-Phe-Arg-Trp-Lys)-NH$_2$ | ND |
| 21 | Ac-Arg-cyclo(Asp-D-Ala-D-Phe-Arg-Trp-Lys)-NH$_2$ | ND |
| 22 | Ac-Arg-cyclo(Asp-D-Ser-D-Phe-Arg-Trp-Lys)-NH$_2$ | ND |
| 23 | Ac-Arg-cyclo(Asp-His-D-Phe-Ala-Trp-Lys)-NH$_2$ | ND |
| 24 | Ac-Arg-cyclo(Asp-His-D-Phe-Nle-Trp-Lys)-NH$_2$ | ND |

-continued

| No. | Amino Acid Sequence | MC4r Ki (nM) |
|---|---|---|
| 25 | Ac-Arg-cyclo(Asp-His-D-Phe-Val-Trp-Lys)-NH$_2$ | ND |
| 26 | Ac-Arg-cyclo(Asp-His-D-Phe-Ser-Trp-Lys)-NH$_2$ | ND |
| 27 | Ac-Arg-cyclo(Asp-Aib-D-Phe-Arg-Trp-Lys)-NH$_2$ | ND |
| 28 | Ac-Arg-cyclo(Asp-Arg-D-Phe-Arg-Trp-Lys)-NH$_2$ | 4* |
| 29 | Ac-Arg-cyclo(Asp-Asn-D-Phe-Arg-Trp-Lys)-NH$_2$ | 32* |
| 30 | Ac-Arg-cyclo(Asp-Asp-D-Phe-Arg-Trp-Lys)-NH$_2$ | ND |
| 31 | Ac-Arg-cyclo(Asp-Glu-D-Phe-Arg-Trp-Lys)-NH$_2$ | ND |
| 32 | Ac-Arg-cyclo(Asp-Gln-D-Phe-Arg-Trp-Lys)-NH$_2$ | 13 |
| 33 | Ac-Arg-cyclo(Asp-Gly-D-Phe-Arg-Trp-Lys)-NH$_2$ | ND |
| 34 | Ac-Arg-cyclo(Asp-Ile-D-Phe-Arg-Trp-Lys)-NH$_2$ | 19* |
| 35 | Ac-Arg-cyclo(Asp-Thr-D-Phe-Arg-Trp-Lys)-NH$_2$ | 140* |
| 36 | Ac-Arg-cyclo(Asp-Trp-D-Phe-Arg-Trp-Lys)-NH$_2$ | 37* |
| 37 | Ac-Arg-cyclo(Asp-D-Val-D-Phe-Arg-Trp-Lys)-NH$_2$ | ND |
| 38 | Ac-Arg-cyclo(Asp-Met-D-Phe-Arg-Trp-Lys)-NH$_2$ | 35* |
| 39 | Ac-Arg-cyclo(Asp-D-Arg-D-Phe-Arg-Trp-Lys)-NH$_2$ | ND |
| 40 | Ac-Arg-cyclo(Asp-D-Asp-D-Phe-Arg-Trp-Lys)-NH$_2$ | ND |
| 41 | Ac-Arg-cyclo(Asp-D-His-D-Phe-Arg-Trp-Lys)-NH$_2$ | 95* |
| 42 | Ac-Arg-cyclo(Asp-D-Leu-D-Phe-Arg-Trp-Lys)-NH$_2$ | ND |
| 43 | Ac-Arg-cyclo(Asp-D-Lys-D-Phe-Arg-Trp-Lys)-NH$_2$ | ND |
| 44 | Ac-Arg-cyclo(Asp-D-Thr-D-Phe-Arg-Trp-Lys)-NH$_2$ | ND |
| 45 | Ac-Arg-cyclo(Asp-D-Trp-D-Phe-Arg-Trp-Lys)-NH$_2$ | ND |
| 46 | Ac-Arg-cyclo(Asp-D-Thr(Bzl)-D-Phe-Arg-Trp-Lys)-NH$_2$ | ND |
| 47 | Ac-Arg-cyclo(Asp-D-Cha-D-Phe-Arg-Trp-Lys)-NH$_2$ | ND |
| 48 | Ac-Arg-cyclo(Asp-Phe(2-C(=O)-NH$_2$)-D-Phe-Arg-Trp-Lys)-NH$_2$ | 23 |
| 49 | Ac-Arg-cyclo(Asp-Phe-(3-(C(=O)-NH$_2$))-D-Phe-Arg-Trp-Lys)-NH$_2$ | 15 |
| 50 | Ac-Arg-cyclo(Asp-Phe(4-(C(=O)-NH$_2$))-D-Phe-Arg-Trp-Lys)-NH$_2$ | 30 |
| 51 | Ac-Arg-cyclo(Asp-His-D-Phe-Arg-Trp-Lys)-OH | 22* |
| 52 | Ac-Arg-cyclo(Asp-Ala-D-Phe-Arg-Trp-Lys)-OH | 144* |
| 53 | Ac-Arg-cyclo(Asp-His-D-Phe-Cit-Trp-Lys)-OH | 214* |
| 54 | Ac-Arg-cyclo(Asp-Hyp(Bzl)-D-Phe-Arg-Trp-Lys)-OH | 3 |
| 55 | Ac-Arg-cyclo(Asp-Pro(Bn)-D-Phe-Arg-Trp-Lys)-OH | 12 |
| 56 | Ac-Arg-cyclo(Asp-Asn-D-Phe-Arg-Trp-Lys)-OH | 100 |
| 57 | Ac-Arg-cyclo(Asp-Gln-D-Phe-Arg-Trp-Lys)-OH | 115 |
| 58 | Ac-Arg-cyclo(Asp-Orn-D-Phe-Arg-Trp-Lys)-OH | 23 |
| 59 | Ac-Arg-cyclo(Asp-Dap-D-Phe-Arg-Trp-Lys)-NH$_2$ | ND |
| 60 | Ac-Arg-cyclo(Asp-His-D-(alpha-Me)Phe-Arg-Trp-Lys)-NH$_2$ | 47* |
| 61 | Ac-Arg-cyclo(Asp-His-(alpha-Me)-Phe-Arg-Trp-Lys)-NH$_2$ | ND |
| 62 | Ac-Arg-cyclo(Asp-Dap-D-Phe-Arg-Trp-Lys)-NH$_2$ | 80* |

-continued

| No. | Amino Acid Sequence | MC4r Ki (nM) |
|---|---|---|
| 63 | Ac-Arg-cyclo(Asp-Sar-D-Phe-Arg-Trp-Lys)-NH$_2$ | 15 |
| 64 | Ac-Arg-cyclo(Glu-His-D-Phe-Arg-Trp-Orn)-NH$_2$ | 1* |
| 65 | Ac-Arg-cyclo(Asp-His-D-Phe-Met(O$_2$)-Trp-Lys)-NH$_2$ | ND |
| 66 | Ac-Arg-cyclo(Asp-His-D-Phe-Gln-Trp-Lys)-NH$_2$ | ND |
| 67 | Ac-Arg-cyclo(Asp-Orn-D-Phe-Arg-Trp-Lys)-NH$_2$ | 7* |
| 68 | Ac-Arg-cyclo(Asp-His-D-Phe-D-Nle-Trp-Lys)-NH$_2$ | ND |
| 69 | Ac-D-Arg-cyclo(Asp-His-D-Phe-Arg-Trp-Lys)-NH$_2$ | 8* |
| 70 | Ac-D-Arg-cyclo(Asp-Ala-D-Phe-Arg-Trp-Lys)-NH$_2$ | 46* |
| 71 | Ac-D-Arg-cyclo(Asp-Gln-D-Phe-Arg-Trp-Lys)-NH$_2$ | 45 |
| 72 | Ac-D-Arg-cyclo(Asp-Pro(4R-Bzl)-D-Phe-Arg-Trp-Lys)-NH$_2$ | 2* |
| 73 | Ac-Arg-cyclo(Asp-Arg-D-Phe-Arg-Trp-Lys)-OH | 60* |
| 74 | Ac-Arg-cyclo(Glu-Gln-D-Phe-Arg-Trp-Orn)-NH$_2$ | 3 |
| 75 | Ac-Arg-cyclo(Orn-His-D-Phe-Arg-Trp-Glu)-NH$_2$ | 0.6 |
| 76 | Ac-Arg-cyclo(Asp-Arg-D-Phe-Arg-Trp-Lys)-NH$_2$ | 14 |
| 77 | Ac-Arg-cyclo(Asp-Met-(O$_2$)-D-Phe-Arg-Trp-Lys)-NH$_2$ | 7 |
| 78 | Ac-Arg-cyclo(Asp-Gln-D-Phe-Arg-Trp-Lys)-NH$_2$ | 86* |
| 79 | Ac-Arg-cyclo(Asp-Hyp-D-Phe-Arg-Trp-Lys)-NH$_2$ | 4 |
| 80 | Ac-Arg-cyclo(Asp-Pro(4R-NH$_2$)-D-Phe-Arg-Trp-Lys)-NH$_2$ | 5 |
| 81 | Ac-Arg-cyclo(Glu-Gln-D-Phe-Arg-Trp-Orn)-OH | 43 |
| 82 | Ac-Arg-cyclo(Glu-His-D-Phe-Arg-Trp-Orn)-OH | 4 |
| 83 | Ac-Arg-cyclo(Orn-Gln-D-Phe-Arg-Trp-Glu)-OH | ND |
| 84 | Ac-Arg-cyclo(Orn-His-D-Phe-Arg-Trp-Glu)-OH | 12* |
| 85 | Ac-D-Arg-cyclo(Glu-His-D-Phe-Arg-Trp-Orn)-OH | 40* |
| 86 | Ac-D-Arg-cyclo(Glu-Gln-D-Phe-Arg-Trp-Orn)-OH | 66* |
| 87 | Ac-D-Arg-cyclo(Glu-Dab-D-Phe-Arg-Trp-Orn)-OH | 171* |
| 88 | Ac-Arg-cyclo(Glu-Arg-D-Phe-Arg-Trp-Orn)-OH | 37* |
| 89 | Ac-Arg-cyclo(Glu-Lys-D-Phe-Arg-Trp-Orn)-OH | 113* |
| 90 | Ac-Arg-cyclo(Glu-Orn-D-Phe-Arg-Trp-Orn)-OH | 9 |
| 91 | Ac-Arg-cyclo(Glu-Asn-D-Phe-Arg-Trp-Orn)-OH | 167 |
| 92 | Ac-Arg-cyclo(Glu-Cit-D-Phe-Arg-Trp-Orn)-OH | 184* |
| 93 | Ac-Arg-cyclo(Asp-Dab(Acetyl)-D-Phe-Arg-Trp-Lys)-NH$_2$ | 33 |
| 94 | Ac-Arg-cyclo(Asp-Dab(Glycly)-D-Phe-Arg-Trp-Lys)-NH$_2$ | 110* |
| 95 | Ac-Arg-cyclo(Asp-Thr-D-Phe-Arg-Trp-Lys)-NH$_2$ | ND |
| 96 | Ac-Arg-cyclo(Lys-His-D-Phe-Arg-Trp-Asp)-NH$_2$ | 1* |
| 97 | Ac-Arg-cyclo(Asp-Phe(4-(C(=O)-NH$_2$))-D-Phe-Arg-Trp-Lys)-OH | ND |
| 98 | Ac-D-Arg-cyclo(Orn-His-D-Phe-Arg-Trp-Glu)-NH$_2$ | 4* |
| 99 | Arg-cyclo(Orn-His-D-Phe-Arg-Trp-Glu)-NH$_2$ | 6 |
| 100 | Ac-Arg-cyclo(Glu-Met(O$_2$)-D-Phe-Arg-Trp-Orn)-NH$_2$ | 8 |
| 101 | Ac-Arg-cyclo(Glu-Hyp-D-Phe-Arg-Trp-Orn)-NH$_2$ | 3 |

-continued

| No. | Amino Acid Sequence | MC4r Ki (nM) |
|---|---|---|
| 102 | Ac-Arg-cyclo(Glu-Arg-D-Phe-Arg-Trp-Orn)-NH$_2$ | 0.7 |
| 103 | Ac-Arg-cyclo(Glu-Lys-D-Phe-Arg-Trp-Orn)-NH$_2$ | 15 |
| 104 | Ac-Arg-cyclo(Glu-Orn-D-Phe-Arg-Trp-Orn)-NH$_2$ | 9* |
| 105 | Ac-Arg-cyclo(Glu-Cit-D-Phe-Arg-Trp-Orn)-NH$_2$ | 6 |
| 106 | Ac-Arg-cyclo(Asp-Gln-D-Phe-Arg-Trp-Lys)-NH-cyclopropyl | 64* |
| 107 | Ac-Arg-cyclo(Glu-Gln-D-Phe-Arg-Trp-Orn)-NH-Et | 34* |
| 108 | Ac-Arg-cyclo(Glu-Gln-D-Phe-Arg-Trp-Orn)-NH-cyclopropyl | 26* |
| 109 | Ac-Arg-cyclo(Glu-His-D-Phe-Arg-Trp-Orn)-NH-Et | 6* |
| 110 | Ac-Arg-cyclo(Glu-His-D-Phe-Arg-Trp-Orn)-NH-cyclopropyl | 1* |
| 111 | Ac-Arg-cyclo(Glu-Met(=O)-D-Phe-Arg-Trp-Orn)-NH$_2$ | 9 |
| 112 | Ac-Arg-cyclo(Glu-Pro(4R-NH$_2$)-D-Phe-Arg-Trp-Orn)-NH$_2$ | 6 |
| 113 | Ac-Arg-cyclo(Asp-Thr(Bzl)-D-Phe-Arg-Trp-Lys)-OH | ND |
| 114 | Ac-Arg-cyclo(Asp-Dab(Acetyl)-D-Phe-Arg-Trp-Lys)-NH$_2$ | 88* |
| 115 | Ac-Arg-cyclo(Asp-His-D-Phe-Cit-Trp-Lys)-NH$_2$ | 87 |
| 116 | Ac-Arg-cyclo(Asp-Lys-D-Phe-Cit-Trp-Lys)-NH$_2$ | 873 |
| 117 | Ac-Arg-cyclo(Asp-Ser-D-Phe-Cit-Trp-Lys)-NH$_2$ | 1446 |
| 118 | Ac-Arg-cyclo(Asp-Dap(betaPro)-D-Phe-Arg-Trp-Lys)-NH$_2$ | 145* |
| 119 | Ac-Arg-cyclo(Orn-Dab-D-Phe-Arg-Trp-Glu)-NH$_2$ | 3* |
| 120 | Ac-Arg-cyclo(Orn-Ala-D-Phe-Arg-Trp-Glu)-NH$_2$ | 19* |
| 121 | Ac-Arg-cyclo(Lys-Dab-D-Phe-Arg-Trp-Asp)-NH$_2$ | 0.4 |
| 122 | Ac-Arg-cyclo(Asp-Dab-D-Phe-Arg-Trp-Lys)-NH-cyclopropyl | 3 |
| 123 | Ac-Arg-cyclo(Asp-Pro(4R-2-Cl-Bzl)-D-Phe-Arg-Trp-Lys)-NH$_2$ | 8* |
| 124 | Ac-Arg-cyclo(Asp-Pro(4R-3-Cl-Bzl)-D-Phe-Arg-Trp-Lys)-NH$_2$ | 19* |
| 125 | Ac-Arg-cyclo(Asp-Pro(4R-4-Cl-Bzl)-D-Phe-Arg-Trp-Lys)-NH$_2$ | 24* |
| 126 | Ac-Arg-cyclo(hGlu-His-D-Phe-Arg-Trp-Dab)-NH$_2$ | 1* |
| 127 | Ac-Arg-cyclo(hGlu-Dab-D-Phe-Arg-Trp-Dab)-NH$_2$ | 2* |
| 128 | Ac-Arg-cyclo(Dab-His-D-Phe-Arg-Trp-hGlu)-NH$_2$ | 2* |
| 129 | Ac-Arg-cyclo(Dab-Dab-D-Phe-Arg-Trp-hGlu)-NH$_2$ | 4* |
| 130 | Ac-Arg-cyclo(Orn-Dab-D-Phe-Arg-Trp-Glu)-OH | 25 |
| 131 | Ac-Arg-cyclo(Lys-Dab-D-Phe-Arg-Trp-Asp)-OH | 35 |
| 132 | Ac-Lys-cyclo(Orn-His-D-Phe-Arg-Trp-Glu)-NH$_2$ | 3* |
| 133 | Ac-D-Lys-cyclo(Orn-His-D-Phe-Arg-Trp-Glu)-NH$_2$ | 8* |
| 134 | Arg-cyclo(Asp-Ser(Bzl)-D-Phe-Arg-Trp-Lys)-OH | 30 |
| 135 | Ac-Lys-cyclo(Asp-His-D-Phe-Arg-Trp-Lys)-NH$_2$ | 9* |
| 136 | Ac-Arg-cyclo(Dab-Dab-D-Phe-Arg-Trp-hGlu)-OH | 35 |
| 137 | Cyclohexanoyl-Arg-cyclo(Asp-Dab-D-Phe-Arg-Trp-Lys)-NH$_2$ | 0.4 |
| 138 | Cyclopentylacetyl-Arg-cyclo(Asp-Dab-D-Phe-Arg-Trp-Lys)-NH$_2$ | 0.8 |
| 139 | Cyclohexylacetyl-Arg-cyclo(Asp-Dab-D-Phe-Arg-Trp-Lys)-NH$_2$ | 1 |

-continued

| No. | Amino Acid Sequence | MC4r Ki (nM) |
|---|---|---|
| 140 | Phenylacetyl-Arg-cyclo(Asp-Dab-D-Phe-Arg-Trp-Lys)-NH$_2$ | 2 |
| 141 | Ac-Cit-cyclo(Asp-Dab-D-Phe-Arg-Trp-Lys)-NH$_2$ | 9 |
| 142 | Ac-Gln-cyclo(Asp-Dab-D-Phe-Arg-Trp-Lys)-NH$_2$ | 15 |
| 143 | Ac-Arg-cyclo(Glu-Dab(Acetyl)-D-Phe-Arg-Trp-Orn)-NH$_2$ | 13 |
| 144 | Ac-Arg-cyclo(hGlu-Dab-D-Phe-Arg-Trp-Dab)-OH | 45 |
| 145 | Ac-Arg-cyclo(hGlu-Met(O$_2$)-D-Phe-Arg-Trp-Dab)-NH$_2$ | 4 |
| 146 | Ac-Arg-cyclo(hGlu-Hyp-D-Phe-Arg-Trp-Dab)-NH$_2$ | 3 |
| 147 | Ac-Arg-cyclo(hGlu-Gln-D-Phe-Arg-Trp-Dab)-NH$_2$ | 20 |
| 148 | Ac-Arg-cyclo(Asp-Orn(Acetyl)-D-Phe-Arg-Trp-Lys)-NH$_2$ | 573 |
| 149 | Ac-Arg-cyclo(Glu-Orn(Acetyl)-D-Phe-Arg-Trp-Orn)-NH$_2$ | 7 |
| 150 | Ac-Arg-cyclo(Orn-Gln-D-Phe-Arg-Trp-Glu)-NH$_2$ | 5 |
| 151 | Ac-Arg-cyclo(Lys-Gln-D-Phe-Arg-Trp-Asp)-NH$_2$ | 4 |
| 152 | Ac-D-Arg-cyclo(Orn-Gln-D-Phe-Arg-Trp-Glu)-NH$_2$ | 6 |
| 153 | n-C4H9-CO-cyclo(Glu-His-D-Phe-Arg-Dab)-Trp-NH$_2$ | 365 |
| 154 | Ac-Arg-cyclo(Orn-Asn-D-Phe-Arg-Trp-Glu)-NH$_2$ | 13 |
| 155 | Ac-Arg-cyclo(Lys-Asn-D-Phe-Arg-Trp-Asp)-NH$_2$ | 5 |
| 156 | Ac-D-Arg-cyclo(Orn-Asn-D-Phe-Arg-Trp-Glu)-NH$_2$ | 28 |
| 157 | Arg-cyclo(Orn-Asn-D-Phe-Arg-Trp-Glu)-NH$_2$ | 42 |
| 158 | Ac-Orn-cyclo(Orn-Asn-D-Phe-Arg-Trp-Glu)-NH$_2$ | 50 |
| 159 | Ac-Arg-cyclo(Dab-Gln-D-Phe-Arg-Trp-hGlu)-NH$_2$ | 4 |
| 160 | Ac-Arg-cyclo(hGlu-Asn-D-Phe-Arg-Trp-Dab)-NH$_2$ | 8 |
| 161 | Ac-Arg-cyclo(Glu-Asn-D-Phe-Arg-Trp-Orn)-NH$_2$ | 6 |
| 162 | Ac-Arg-cyclo(Lys-Asn-D-Phe-Arg-Nal2-Asp)-NH$_2$ | 5 |
| 163 | Ac-Arg-cyclo(Asp-Dab-D-Phe-Arg-Trp-Lys)-NH$_2$ | 4 |
| 164 | Ac-Arg-cyclo(Asp-Dab-D-Phe-Arg-Trp-Lys)-OH | 57 |
| 165 | Ac-Arg-cyclo(Glu-Dab-D-Phe-Arg-Trp-Orn)-NH$_2$ | 0.65 |
| 166 | Ac-Arg-cyclo(Glu-Dab-D-Phe-Arg-Trp-Orn)-OH | 8 |

2. The peptides of Nos. 126 through 129 were tested in functional assays. The peptide No. 126 was determined to be an agonist at MC4r, with intrinsic activity of 101% at MC4r where NDP-α-MSH is 100%, and with an $EC_{50}$ of 0.047 nM (average of three studies). The peptide No. 127 was determined to be an agonist at MC4r, with intrinsic activity of 98% at MC4r where NDP-α-MSH is 100%, and with an $EC_{50}$ of 0.06 nM (average of two studies). The peptide No. 128 was determined to be an agonist at MC4r, with intrinsic activity of 95% at MC4r where NDP-α-MSH is 100%, and with an $EC_{50}$ of 0.073 nM (average of three studies). The peptide No. 129 was determined to be an agonist at MC4r, with intrinsic activity of 96% at MC4r where NDP-α-MSH is 100%, and with an $EC_{50}$ of 0.065 nM (average of two studies). Thus for the four peptides in the series, $EC_{50}$ values were on the order of one and one-half-fold to two-fold less that the Ki values.

3. Peptide No. 1 was evaluated for binding against MC1r, MC3r and MC4r in competitive studies using Eu-labeled NDP-α-MSH, and was found to have a Ki value of 4 nM at MC4r (average of six studies), a Ki value of 4 nM for MC1r (average of four studies) and a Ki value of 103 nM for MC3r (average of five studies). In competitive studies using [I$^{125}$]-NDP-α-MSH, peptide No. 1 was found to have a Ki value of 2 nM at MC4r (one study), 25 nM at MC3r (one study) and 3 nM at MC1r (one study). In functional studies, Peptide No. 1 was determined to be an agonist, with intrinsic activity of 91% at MC4r where NDP-α-MSH is 100%, and with an $EC_{50}$ of 1 nM (average of three studies).

In rat feeding studies, using bremelanotide (a non-specific MC4r agonist of the formula Ac-Nle-cyclo(Asp-His-D-Phe-Arg-Trp-Lys)-OH)) as a positive control, peptide No. 1 was found to reduce food intake and decrease the rate of change in body weight. Using the methods as described above, groups of 8 rats each rats received 1 mg/kg bremelanotide, 0.3 mg/kg of peptide No. 1, 1 mg/kg of peptide No. 1 or vehicle control. For the 0-2, 0-4, and 0-20 hour periods, the decrease in food consumption in rats receiving either 0.3 or 1 mg/kg of peptide No. 1 was statistically significant compared to control. The 0-20 hour percent change in body weight was also statistically significant compared to control for the group receiving 1 mg/kg of peptide No. 1.

4. Peptide No. 16 was evaluated for binding against MC1r, MC3r and MC4r in competitive studies using Eu-labeled NDP-α-MSH, and was found to have a Ki value of 25 nM at MC4r (average of two studies), a Ki value of 323 nM for MC1r (one study) and a Ki value of 1055 nM for MC3r (one study). In functional studies, Peptide No. 16 was determined to be a partial agonist, with intrinsic activity of 42% at MC4r where NDP-α-MSH is 100%, and with an $EC_{50}$ of 40 nM (average of five studies).

In rat feeding studies, using bremelanotide as a positive control, peptide No. 16 was found to reduce food intake and decrease the rate of change in body weight. Using the methods as described above, groups of 8 rats each rats received 1 mg/kg bremelanotide, 0.3 mg/kg of peptide No. 16, 1 mg/kg of peptide No. 16 or vehicle control. For the 0-2, 0-4, and 0-20 hour periods, the decrease in food consumption in rats receiving 1 mg/kg of peptide No. 16 was statistically significant compared to control, and for the 0-2 and 0-4 hour periods, the decrease in food consumption in rats receiving 0.3 mg/kg of peptide No. 16 was statistically significant compared to control. The 0-20 hour percent change in body weight was also statistically significant compared to control for the group receiving 1 mg/kg of peptide No. 16.

5. Peptide No. 32 was evaluated for binding against MC1r and MC4r in competitive studies using Eu-labeled NDP-α-MSH, and was found to have a Ki value of 24 nM at MC4r (average of six studies) and a Ki value of 673 nM for MC1r (average of three studies). In competitive studies using $[I^{125}]$-NDP-α-MSH, peptide No. 32 was found to have a Ki value of 13 nM at MC4r (two studies), 340 nM at MC3r (one study) and 133 nM at MC1r (two studies). In functional studies, Peptide No. 32 was determined to be an agonist, with intrinsic activity of 98% at MC4r where NDP-α-MSH is 100%, and with an $EC_{50}$ of 17 nM (average of eight studies).

6. Certain peptides were tested for binding selectivity (Ki) to MC1r and MC4r, and also for functional selectivity ($EC_{50}$ and intrinsic activity, referred to as "$E_{max}$" below) to both MC1r and MC4r, with the results as shown below:

| Peptide No. | hMC4r (Ki) (nM) | hMC1r (Ki) (nM) | hMC4r $EC_{50}$ (nM) | hMC4r $E_{max}$ (%) | hMC1r $EC_{50}$ (nM) | hMC1r $E_{max}$ (%) |
|---|---|---|---|---|---|---|
| 71 | 45 | 3350 | 2 | 89 | 60 | 88 |
| 150 | 5 | 130 | 0.3 | 87 | 9 | 89 |
| 152 | 6 | 120 | 0.5 | 89 | 18 | 85 |
| 154 | 13 | 688 | 0.625 | 87 | 25 | 87 |
| 155 | 5 | 240 | 0.189 | 97 | 14 | 91 |
| 156 | 28 | 840 | 2 | 89 | 80 | 81 |
| 159 | 4 | 133 | 0.825 | 99 | 26 | 98 |
| 160 | 8 | 295 | 0.245 | 98 | 18 | 95 |
| 161 | 6 | 155 | 0.413 | 91 | 13 | 85 |
| 162 | 5 | 255 | 0.85 | 82 | 22 | 89 |

Thus while each of the foregoing peptides is an agonist at both MC1r and MC4r (defined as 70% or greater intrinsic activity), in all instances both binding selectivity and functional selectivity was at least twenty times more specific at MC4r than at MC1r.

7. Peptide Nos. 154 and 155 were evaluated in pharmacokinetic studies, and in a rat model with subcutaneous injection of the formulation as in Section 9.7, each had a terminal half-life of approximately 0.7 hours.

8. Peptide No. 154 was evaluated with GLP-1 (Alfa Aesar, catalog J66197, GLP-1 (7-36) amide, human) to determine effect on body weight and feed intake in diet induced obese mice. Diet induced obese mice were divided into groups and subcutaneously implanted with Alzet continuous infusion pumps containing one of the following formulations:
  Group 1: Vehicle
  Group 2: 30 mg/kg/day Peptide No. 154 (MC4r 154) by bolus administration
  Group 3: 0.1 mg/kg/day GLP-1 by continuous infusion
  Group 4: 30 mg/kg/day MC4r 154 by bolus administration and 0.1 mg/kg/day GLP-1 by continuous infusion Groups 1, 2 and 4 were provided ad libitum with a 45% high fat rodent diet. Animals in Group 3 were pair-fed to Group 2. The amount of food consumed in Group 2 was the amount of food given to Group 3 in the next 24 hour period. For group 3 (pair-fed group), the pump was implanted 1 day later than other groups to account for pair-feeding. On day −2 and day 6, animals from Groups 1, 2, and 4 were fasted overnight and baseline and terminal glucose tolerance tests (GTT) was conducted. GTT and insulin levels in Group 3 were conducted one day later. Body weight and food intake were measured each day. To conduct the GTT, on study day −2 (−1 for Group 3) (baseline test) and day 6 (7 for Group 3) (termination test), 1 g/kg glucose was orally administered. Glucose levels were taken prior to glucose administration and 15, 30, 60, 90 and 120 minutes post-glucose administration.

FIG. 1 shows the percent change in the area under the curve (AUC) for the GTT from the baseline test to the termination test. Data is expressed as percent change at the termination test, ±standard deviation (SD) from the baseline test. This was calculated as:

$$(AUC_{day\ 7} - AUC_{day\ -2})/AUC_{day\ 7}$$

In FIG. 1, diet induced obese mice were administered MC4r 154 (30 mg/kg/day) either with or without 0.1 mg/kg/day GLP-1, with one group pair fed to the MC4r 154 group but administered only GLP-1 ("Pair-Fed to MC4r 154+GLP-1").

Figure 2:
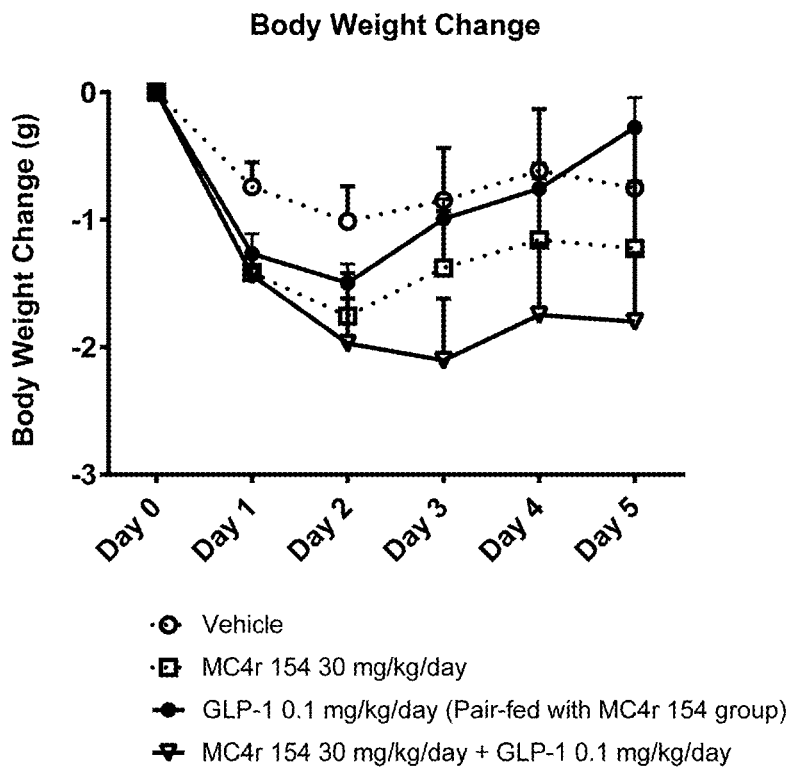
FIG. 2 depicts average body weight change in grams in DIO mice from study day 0 through study day 5 in DIO mice administered vehicle, MC4r 154, combinations of MC4r 154 and GLP-1, or GLP-1 combined with a caloric restriction to mimic food intake with MC4r 154, ±standard error of the mean (SEM). All compounds were administered via subcutaneous osmotic pump on study days 0 to 5. For combination therapy the agents were co-formulated into one solution and administered via a single osmotic pump. For the GLP-1 caloric restriction group the pump implantation was delayed by one day and the amount of food given to the animals was matched to those receiving MC4r 154 alone. Body weight was measured daily prior to beginning of the feeding cycle.

FIG. 2 shows the body weight change from study day 0 (day prior to initiation of administration of formulations) through study day 5. Data is shown as the average of body weight change in grams±standard error of the mean (SEM) from study day 0. As is shown in FIG. 2, the greatest weight loss was seen in Group 4, which was concurrently administered both MC4r 154 and GLP-1. Virtually no change in weight was seen in Group 3, which was administered only GLP-1 and was pair-fed with Group 2.

9. MC4r 154 was evaluated with GLP-1 to determine effect on body weight and feed intake in diet induced obese Sprague-Dawley rats. Rats were acquired at 17 weeks and pre-conditioned for 5 weeks on high fat diet prior to dosing. No sharp increase in weight was noted, likely due to late onset of the high fat diet. At study day −2, baseline GTT and insulin levels were assessed on 16-hour fasted animals. Animals were then permitted a 2-day recovery period, and on study day 0, animals were randomized into treatment groups by body weight and Alzet continuous infusion pumps containing either vehicle or GLP-1 (for dosing at either 10 or 100 μg/kg/day) were implanted. Beginning on study day 1, body weight and feed weights were taken in the mornings. Beginning on study day 4, twice daily (b.i.d.) subcutaneous dosing of saline was initiated for all groups other than the treatment naïve group to acclimate the animals to handling and subcutaneous dosing. Beginning on study day 7, and through study day 11, all groups other than treatment naïve, vehicle control and GLP-1 only groups were administered a bolus injection of either 0.1 or 1 mg/kg of Peptide No. 154 b.i.d., with the final dose of Peptide No. 154 on study day 12, one hour prior to GTT and insulin testing. Animals were fasted for the 16 hours prior to the GTT.

Figure 3:
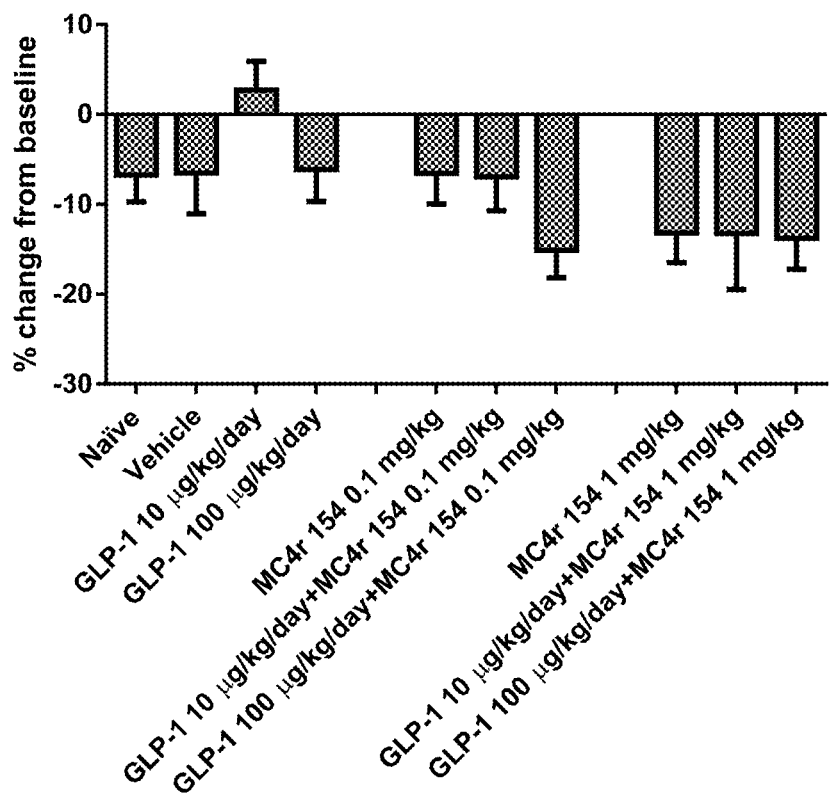
FIG. 3 depicts percent change in glucose from the baseline test (study day −2) to the termination test (study day 12) in DIO Sprague-Dawley rats, ±SEM, with animals receiving vehicle, MC4r 154, GLP-1 or combinations of MC4r 154 and GLP-1 as depicted. GLP-1 was administered via subcutaneously implanted osmotic pump on study days 0 to 12. MC4r 154 was administered twice daily via subcutaneous injection on study days 7 through 12.

FIG. 3 shows the percent change for the glucose test from the baseline test (study day −2) to the termination test (study day 12, after 16 hour fast and prior to GTT testing). Data is shown as the percent change from study day −2 baseline test±SEM. As show in FIG. 3, there was little or no change in glucose levels in groups receiving only GLP-1. The most pronounced decrease in fasted plasma glucose was seen in animals receiving 100 μg/kg/day GLP-1 and a bolus injection of 0.1 mg/kg Peptide No. 154 b.i.d., and in animals receiving a bolus injection of 1.0 mg/kg Peptide No. 154 b.i.d, either alone or with either 10 or 100 μg/kg/day GLP-1.

Figure 4:
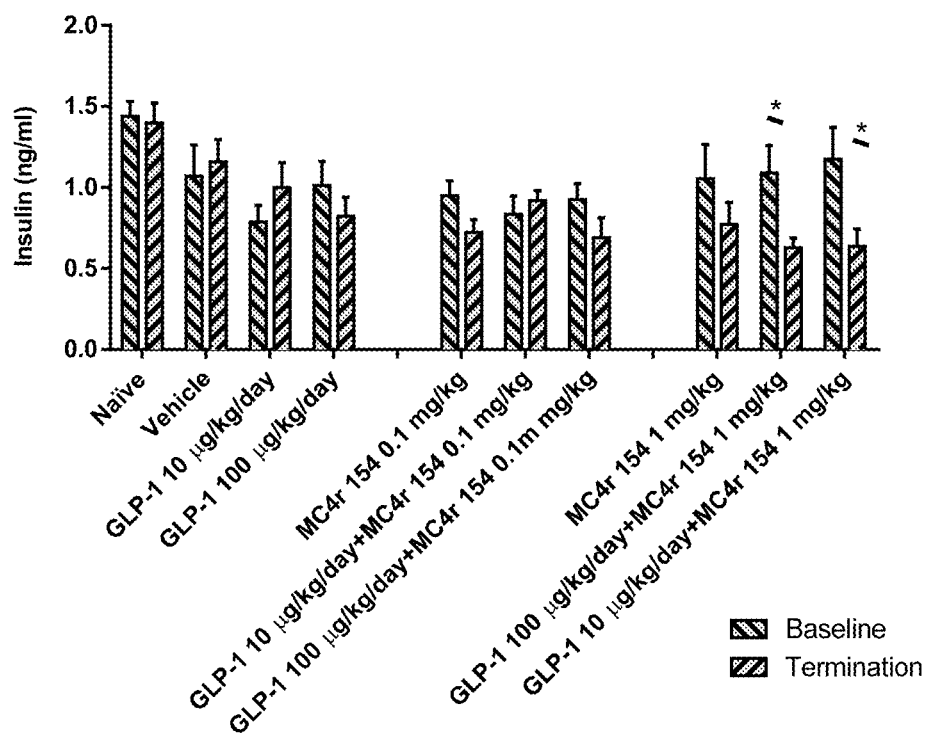
FIG. 4 depicts fasted insulin levels from the baseline test (study day −2) to termination test (study day 12) in ng/mL insulin±SEM, with animals receiving vehicle, MC4r 154, GLP-1 or combinations of MC4r 154 and GLP-1 as depicted. GLP-1 was administered via subcutaneously implanted osmotic pump on study days 0 to 12. MC4r 154 was administered twice daily via subcutaneous injection on study days 7 through 12.

FIG. 4 compares the fasted insulin levels at study day −2 and study day 12, with insulin measured after 16 hour fast and prior to GTT testing. Data is shown as ng/mL insulin±SEM. As can be seen, the most pronounced decrease in insulin levels from study day −2 to study day 12 (p-value<0.05, as shown by the asterisk) was seen in groups receiving GLP-1 at either 10 or 100 μg/kg/day in combination with the bolus injection of 1.0 mg/kg Peptide No. 154 b.i.d.

10. In other studies, it was observed that even in the absence of a GLP-1 receptor agonist that subcutaneous bolus injection of Peptide No. 154 resulted in greater weight loss, and continued weight loss over time, compared to continuous infusion of Peptide No. 154. Weight loss was compared between Group 2 in Example 8 above, in which DIO mice received continuous infusion of 30 mg/kg/day, and a study in which DIO mice received 3 mg/kg of Peptide No. 154 in a single daily bolus dose. As shown in FIG. 2, with continuous infusion of 30 mg/kg/day animals lost weight only for the first two days, and reached a maximum weight loss of 1.76 g±0.34 SEM compared to baseline (study day 0). By contrast, animals receiving a single daily subcutaneous dose of 3 mg/kg continuously lost weight over 5 days, and reached a maximum weight loss on day 5 of 4.2 g±0.6 SEM compared to baseline (study day 0).

11. Peptide No. 154 was evaluated with GLP-1 (GenScript) to determine effect on body weight and feed intake in diet induced obese rats. Rats were implanted with an Azlet pump 2ML2 at day 0, and received continuous infusion of GLP-1 (at a concentration of 1.5 mg/mL for the 300 μg/kg/day dose and a concentration of 5 mg/mL for the 1000 μg/kg/day dose) or vehicle (3.2% mannitol and 50 mM Tris in deionized water, pH 7.4) on study days 0 through 10, and twice daily subcutaneous injection of Peptide No. 154 at a dose of 0.3, 1.0 or 3.0 mg/kg or vehicle in a volume of 1.2 mL vehicle on days 5 through 10. The rats were divided into the following groups
  Group 1: Sham
  Group 2: Vehicle
  Group 3: 1000 μg/kg/day continuous infusion GLP-1 and 0.3 mg/kg Peptide No. 154 by bolus subcutaneous administration twice daily
  Group 4: 1000 μg/kg/day continuous infusion GLP-1 and 1.0 mg/kg Peptide No. 154 by bolus subcutaneous administration twice daily
  Group 5: 1000 μg/kg/day continuous infusion GLP-1 and 3.0 mg/kg Peptide No. 154 by bolus subcutaneous administration twice daily
  Group 6: 300 μg/kg/day continuous infusion GLP-1 and 0.3 mg/kg Peptide No. 154 by bolus subcutaneous administration twice daily
  Group 7: 300 μg/kg/day continuous infusion GLP-1 and 1.0 mg/kg Peptide No. 154 by bolus subcutaneous administration twice daily
  Group 8: 300 μg/kg/day continuous infusion GLP-1 and 3.0 mg/kg Peptide No. 154 by bolus subcutaneous administration twice daily
  Group 9: 1000 μg/kg/day continuous infusion GLP-1
  Group 10: 300 μg/kg/day continuous infusion GLP-1
  Group 11: 0.3 mg/kg Peptide No. 154 by bolus subcutaneous administration twice daily
  Group 12: 1.0 mg/kg Peptide No. 154 by bolus subcutaneous administration twice daily
  Group 13: 3.0 mg/kg Peptide No. 154 by bolus subcutaneous administration twice daily All data was calculated as means±SEM. Each treatment group was compared to the vehicle group using t-test, one-way ANOVA or two-way ANOVA followed by Dunnett's multiple comparisons (GraphPad). A p value<0.05 was considered to represent a significant difference.

Individual body weights were measured on study days 1-9. Percent change in body weight is calculating according to this formula: 100*(value-baseline)/baseline, where value is the weight of the animal on study day in question and baseline is the weight of the same animal on study day −1. Compared with vehicle, subcutaneous dosing of Peptide No. 154 decreased animal's body weight significantly. Combination of continuous infusion of GLP-1 at dose of 1000 μg/kg/day with Peptide No. 154 showed more decrease in body weight.

On days 1-4, feeds were weighed at 0, and 24 hours after lights off. On days 5-9, feeds were weighed at 0, 2, 6 and 24 hours after lights off. Compared with vehicle, there was no significant difference on feed intake with continuous infusion of GLP-1. Food intake decreased starting on day 5 following subcutaneous dosing of Peptide No. 154 in both groups receiving only Peptide No. 154 and groups receiving a combination of GLP-1 and Peptide No. 154. Appetites in groups receiving only Peptide No. 154 recovered on day 9, but remained decreased in groups receiving a combination of GLP-1 and Peptide No. 154. At 2 and 6 hours post lights off, both groups receiving only Peptide No. 154 and groups receiving a combination of GLP-1 and Peptide No. 154 showed significant decreased feed intakes compared with the vehicle group.

Figure 6:
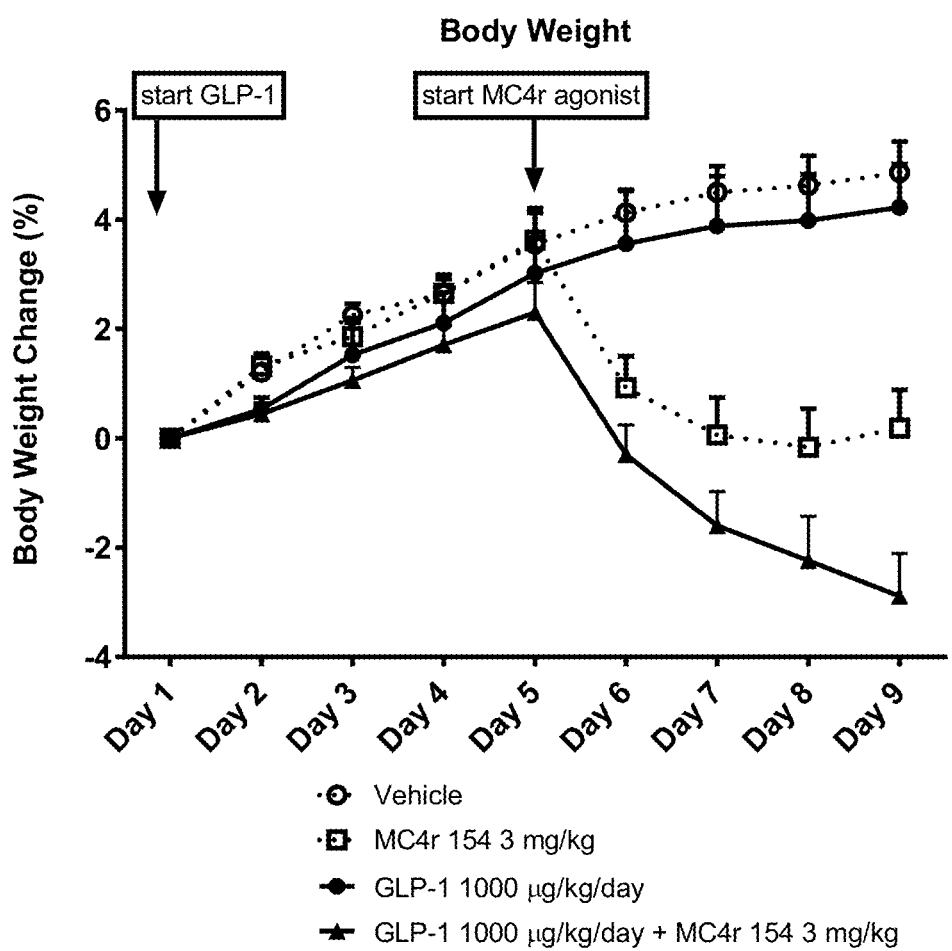
FIGS. 6 through 8 depict average body weight change in percent of baseline in DIO rats from study day 0 through study day 9 in DIO rats administered vehicle, MC4r 154, or a combination of MC4r 154 and GLP-1 on study day 5, at the doses depicted in FIGS. 6 through 8. GLP-1 was administered via subcutaneously implanted osmotic pump on study days 0 to 10. MC4r 154 was administered twice daily via subcutaneous injection on study days 5 through 10. Body weight was measured daily prior to the beginning of the feeding cycle and prior to the first dose of MC4r 154.

FIG. 6 shows average body weight change in percent of baseline in DIO rats from study day 0 through study day 9 in DIO rats administered vehicle, 1000 μg/kg/day of GLP-1, 3 mg/kg MC4r 154, or a combination of MC4r 154 and GLP-1. GLP-1 was administered via subcutaneously implanted osmotic pump on study days 0 to 10. MC4r 154 was administered twice daily via subcutaneous injection on study days 5 through 10. Body weight was measured daily prior to beginning of the feeding cycle and prior to the first dose of MC4r 154.

Figure 7:
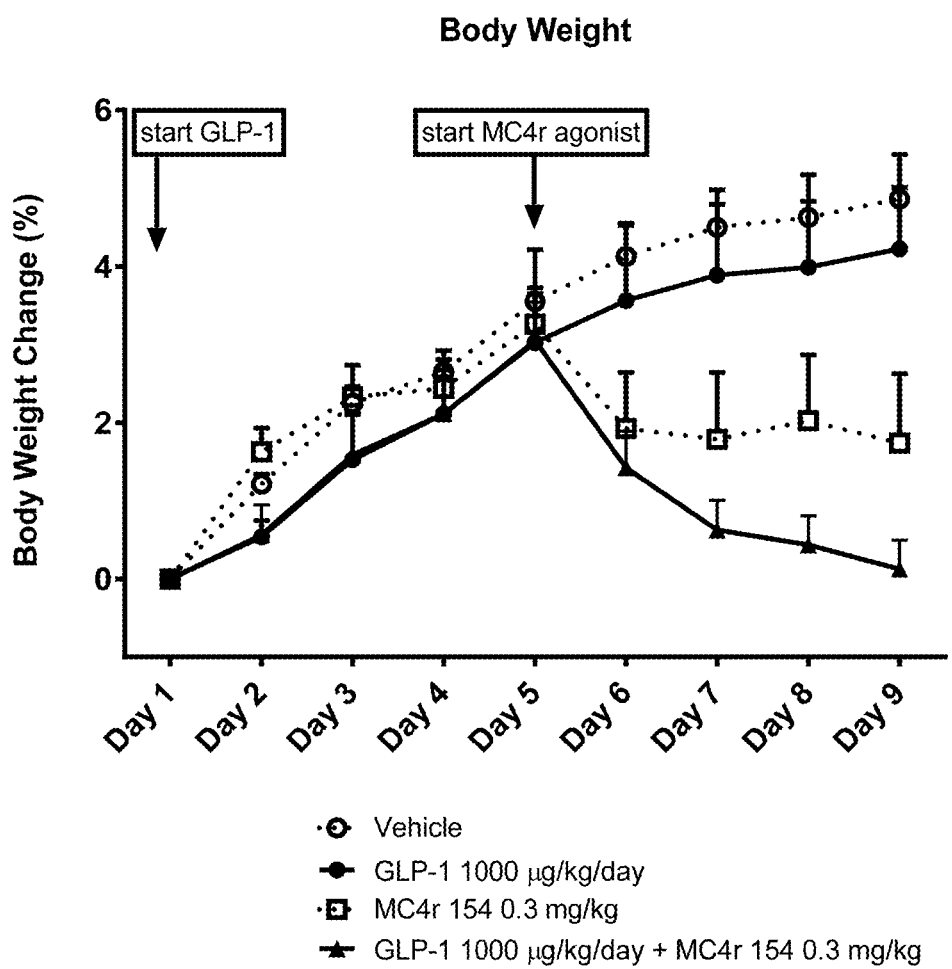

FIG. 7 shows average body weight change in percent of baseline in DIO rats from study day 0 through study day 9 in DIO rats administered vehicle, 1000 μg/kg/day of GLP-1, 0.3 mg/kg MC4r 154, or a combination of MC4r 154 and GLP-1. GLP-1 was administered via subcutaneously implanted osmotic pump on study days 0 to 10. MC4r 154 was administered twice daily via subcutaneous injection on study days 5 through 10. Body weight was measured daily prior to beginning of the feeding cycle and prior to the first dose of MC4r 154.

Figure 8:
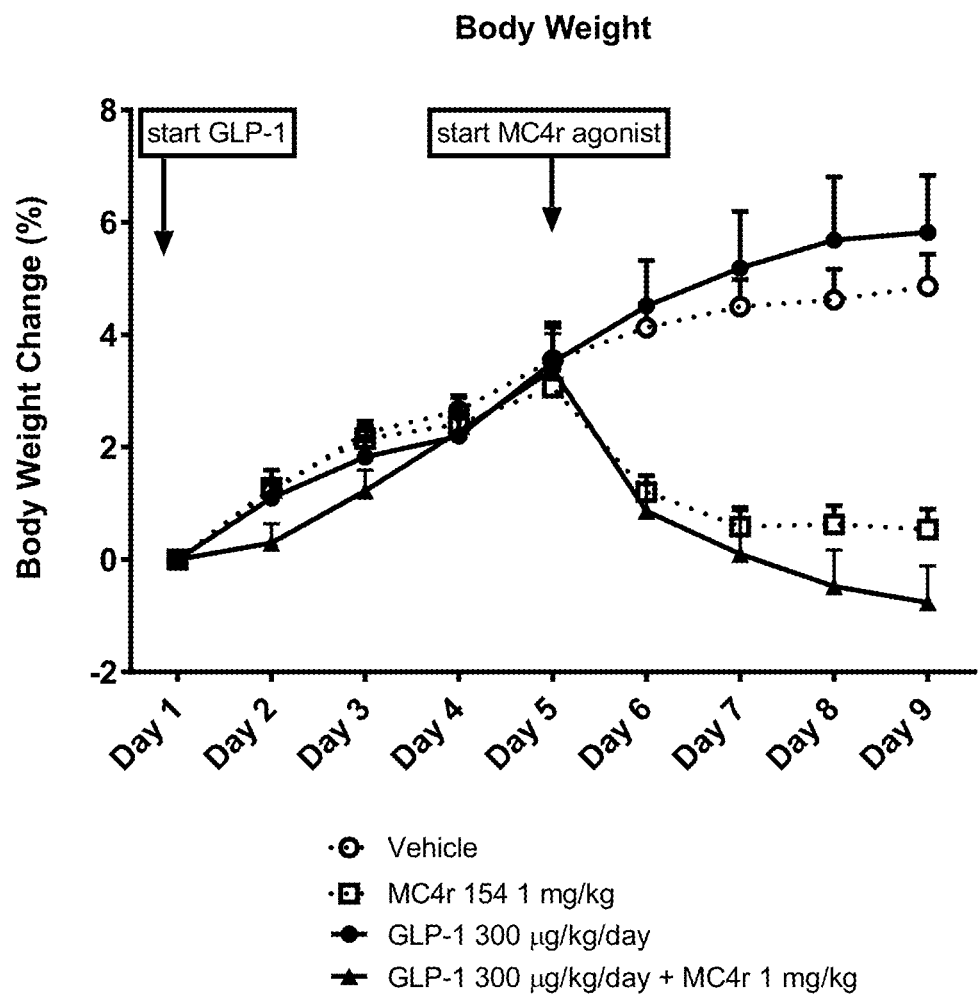

FIG. 8 shows average body weight change in percent of baseline in DIO rats from study day 0 through study day 9 in DIO rats administered vehicle, 300 µg/kg/day of GLP-1, 1 mg/kg MC4r 154, or a combination of MC4r 154 and GLP-1. GLP-1 was administered via subcutaneously implanted osmotic pump on study days 0 to 10. MC4r 154 was administered twice daily via subcutaneous injection on study days 5 through 10. Body weight was measured daily prior to beginning of the feeding cycle and prior to the first dose of MC4r 154.

Figure 5:
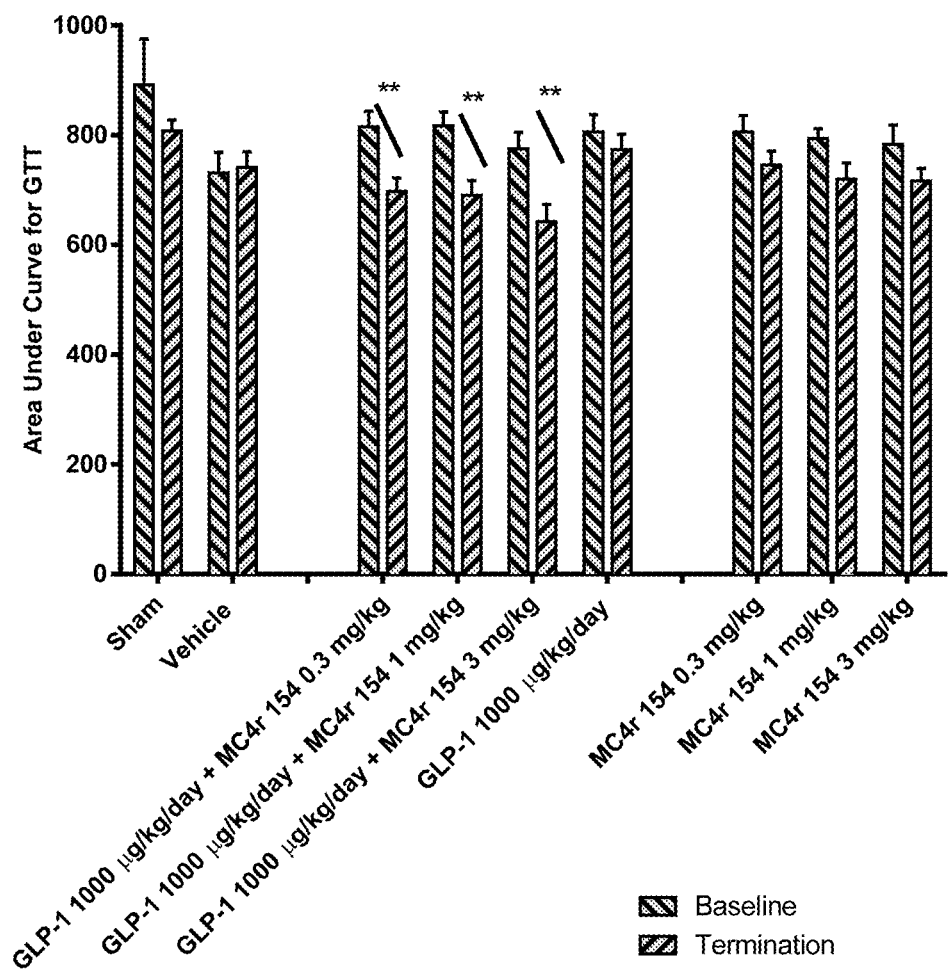
FIG. 5 depicts percent change in the AUC for a glucose tolerance test from the baseline test (study day −2) to the termination test (study day 10) for DIO rats administered vehicle, an MC4r agonist (MC4r 154), or a combination of MC4r agonist and GLP-1. GLP-1 was administered via subcutaneously implanted osmotic pump on study days 0 to 10. MC4r agonist was administered twice daily via subcutaneous injection on study days 5 through 10.

12. In the study of Example 11 above, on day −2 (baseline) and day 10 (termination), glucose was administered at 1 g/kg orally to each animal. Glucose levels were taken on baseline (prior to glucose) and 15, 30, 60, 90 and 120 minutes post glucose administration. As shown in FIG. 5, after 10 days of treatment, compared with baseline level, only groups receiving a combination of GLP-1 and Peptide No. 154 showed a significant inhibition of blood glucose level ($p<0.01$). FIG. 5 shows percent change in the AUC for a glucose tolerance test from the baseline test to the termination test with DIO rats administered vehicle, MC4r 154, or a combination of MC4r 154 and GLP-1. GLP-1 was administered via subcutaneously implanted osmotic pump on study days 0 to 10. MC4r 154 was administered twice daily via subcutaneous injection on study days 5 through 10.

13. Formulations are made consisting of the following active ingredients per dose:

| Formulation | GLP-1 Agonist | MC4r Agonist |
|---|---|---|
| 13.1 | 0.6 mg liraglutide | 1.0 mg Peptide 154 |
| 13.2 | 0.6 mg liraglutide | 1.75 mg Peptide 154 |
| 13.3 | 0.6 mg liraglutide | 5.0 mg Peptide 154 |
| 13.4 | 0.6 mg liraglutide | 10.0 mg Peptide 154 |
| 13.5 | 1.5 mg liraglutide | 1.0 mg Peptide 154 |
| 13.6 | 1.5 mg liraglutide | 1.75 mg Peptide 154 |
| 13.7 | 1.5 mg liraglutide | 5.0 mg Peptide 154 |
| 13.8 | 1.5 mg liraglutide | 10.0 mg Peptide 154 |

The exenatide and Peptide 154 are free-base and anhydrous weights. Each dose unit is supplied for subcutaneous injection in a sterile, preserve isotonic solution in a volume of between 0.3 and 0.5 mL, which also optionally includes metacresol as an antimicrobial preservative, mannitol as a tonicity-adjusting agent, and glacial acetic acid and sodium acetate trihydrate in water for injection as a buffering solution at pH 4.5.

Any of the formulations 13.1 through 13.8 are administered to patients in need of treatment of obesity or to induce weight loss, or to patients in need of improved glycemic control, by once daily subcutaneous injection.

14. A formulation is made consisting of the following active ingredients per dose:

| Formulation | GLP-1 Agonist | MC4r Agonist |
|---|---|---|
| 14.1 | 5 µg extenatide | 1.0 mg Peptide 154 |
| 14.2 | 5 µg extenatide | 1.75 mg Peptide 154 |
| 14.3 | 5 µg extenatide | 2.5 mg Peptide 154 |
| 14.4 | 5 µg extenatide | 150 mg Peptide 154 |
| 14.5 | 10 µg extenatide | 1.0 mg Peptide 154 |
| 14.6 | 10 µg extenatide | 1.75 mg Peptide 154 |
| 14.7 | 10 µg extenatide | 2.5 mg Peptide 154 |
| 14.8 | 10 µg extenatide | 5.0 mg Peptide 154 |
| 14.9 | 20 µg extenatide | 1.0 mg Peptide 154 |
| 14.10 | 20 µg extenatide | 1.75 mg Peptide 154 |
| 14.11 | 20 µg extenatide | 2.5 mg Peptide 154 |
| 14.12 | 20 µg extenatide | 5.0 mg Peptide 154 |

The liraglutide and Peptide 154 are free-base and anhydrous weights. Each dose unit is supplied for subcutaneous injection in a sterile, preserve isotonic solution in a volume of between 0.3 and 0.5 mL, which optionally also includes disodium phosphate dihydrate, propylene glycol, phenol, and water for injection.

Any of the formulations 14.1 through 14.12 are administered to patients in need of treatment of obesity or to induce weight loss, or to patients in need of improved glycemic control, by twice daily subcutaneous injection, preferably at least one hour prior to breakfast and dinner.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

We claim:

1. A method of treating a patient with obesity, comprising administering to the patient (a) a melanocortin receptor-4 agonist in a quantity sufficient to induce at least minimal weight loss when administered as a monotherapy not in conjunction with a glucagon-like peptide-1 receptor agonist and (b) a glucagon-like peptide-1 receptor agonist in a quantity sufficient to induce glycemic control but not weight loss when administered as a monotherapy not in conjunction with a melanocortin receptor-4 agonist, wherein the method elicits a synergistic effect on treatment of obesity.

2. The method of claim 1 wherein the quantity and schedule of administration of the melanocortin receptor-4 agonist and the glucagon-like peptide-1 receptor agonist are together sufficient to produce synergistic effect in the treatment of obesity.

3. A method of treating a patient with obesity, diabetes or metabolic syndrome, comprising administering to the patient (a) a melanocortin receptor-4 agonist in a quantity sufficient to induce at least minimal weight loss when administered as a monotherapy not in conjunction with a glucagon-like peptide-1 receptor agonist and (b) a glucagon-like peptide-1 receptor agonist in a quantity sufficient to induce glycemic control but not weight loss when administered as a monotherapy not in conjunction with a melanocortin receptor-4 agonist, wherein the method elicits a synergistic effect on treatment of glycemic control.

4. The method of claim 1 or 3 wherein the glucagon-like peptide-1 receptor agonist is administered by subcutaneous injection.

5. The method of claim 4 wherein the glucagon-like peptide-1 receptor agonist is liraglutide or exenatide administered daily or twice daily.

6. The method of claim 4 wherein the glucagon-like peptide-1 receptor agonist is lixisenatide, albiglutide, dulaglutide or an extended release formulation of exenatide or liraglutide administered at weekly or greater intervals.

7. The method of claim 1 wherein the melanocortin receptor-4 agonist and the glucagon-like peptide-1 receptor agonist are administered simultaneously to the patient.

8. The method of claim 1 wherein the melanocortin receptor-4 agonist and the glucagon-like peptide-1 receptor agonist are administered sequentially to the patient in either order.

9. The method of claim 1 wherein the melanocortin receptor-4 agonist and the glucagon-like peptide-1 receptor agonist are administered to the patient via different pathways of administration.

10. The method of claim 1 wherein the melanocortin receptor-4 agonist comprises a sustained-release melanocortin receptor-4 agonist.

11. The method of claim 1 or 3 wherein the glucagon-like peptide-1 receptor agonist comprises a sustained-release glucagon-like peptide-1 receptor agonist.

12. The method of claim 11 wherein the sustained-released glucagon-like peptide-1 receptor agonist has a duration of action of at least about twenty-four hours.

13. The method of claim 11 wherein the duration of action is at least about one week.

14. The method of claim 11 wherein the duration of action is at least about two weeks.

15. The method of claim 11 wherein the melanocortin receptor-4 agonist is not sustained-release.

16. The method of claim 1 or 3 wherein the melanocortin receptor-4 agonist is Ac-Arg-cyclo(Orn-Asn-D-Phe-Arg-Trp-Glu)-NH$_2$ administered daily by subcutaneous injection.

17. The method of claim 3 wherein the quantity and schedule of administration of the melanocortin receptor-4 agonist and the glucagon-like peptide-1 receptor agonist are together sufficient to produce synergistic effect in the treatment of glycemic control.

* * * * *